US011213496B2

(12) United States Patent
Zhang

(10) Patent No.: US 11,213,496 B2
(45) Date of Patent: *Jan. 4, 2022

(54) METHODS OF USING DIPIVEFRIN

(71) Applicant: Insignis Therapeutics, Inc., North Haven, CT (US)

(72) Inventor: Mingbao Zhang, Millwood, NY (US)

(73) Assignee: INSIGNIS THERAPEUTICS, INC., North Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/126,766

(22) Filed: Sep. 10, 2018

(65) Prior Publication Data
US 2019/0076378 A1 Mar. 14, 2019

Related U.S. Application Data

(60) Provisional application No. 62/555,854, filed on Sep. 8, 2017.

(51) Int. Cl.
| | | |
|---|---|---|
| *A61K 31/37* | (2006.01) | |
| *A61K 9/00* | (2006.01) | |
| *A61K 47/38* | (2006.01) | |
| *A61K 47/42* | (2017.01) | |
| *A61P 11/00* | (2006.01) | |
| *A61P 11/06* | (2006.01) | |
| *A61P 11/16* | (2006.01) | |
| *A61P 31/00* | (2006.01) | |
| *A61P 31/04* | (2006.01) | |
| *A61P 35/00* | (2006.01) | |
| *A61P 37/00* | (2006.01) | |
| *A61P 37/08* | (2006.01) | |
| *A61K 31/222* | (2006.01) | |
| *A61P 31/16* | (2006.01) | |
| *A61K 31/137* | (2006.01) | |

(52) U.S. Cl.
CPC .......... *A61K 31/137* (2013.01); *A61K 9/0056* (2013.01); *A61K 47/38* (2013.01); *A61K 47/42* (2013.01); *A61P 11/00* (2018.01); *A61P 11/06* (2018.01); *A61P 11/16* (2018.01); *A61P 31/00* (2018.01); *A61P 31/04* (2018.01); *A61P 35/00* (2018.01); *A61P 37/00* (2018.01); *A61P 37/08* (2018.01)

(58) Field of Classification Search
CPC .... A61K 31/137; A61K 9/0056; A61K 47/38; A61K 47/42; A61P 37/00; A61P 31/00; A61P 11/06; A61P 37/08; A61P 31/04; A61P 11/00; A61P 11/16; A61P 35/00
See application file for complete search history.

(56) References Cited

U.S. PATENT DOCUMENTS

| | | | | |
|---|---|---|---|---|
| 3,809,714 | A | * | 5/1974 | Hussain et al. ......... A61P 27/02 560/142 |
| 3,839,584 | A | | 10/1974 | Hussain et al. |
| 3,868,461 | A | | 2/1975 | Hussain et al. |
| 4,035,405 | A | | 7/1977 | Bodor et al. |
| 4,085,270 | A | * | 4/1978 | Henschler ............... C07C 51/14 560/105 |
| 4,094,983 | A | | 6/1978 | Bodor |
| 4,145,441 | A | | 3/1979 | Bodor |
| 4,180,586 | A | | 12/1979 | Eriksen |
| 5,567,439 | A | | 10/1996 | Myers et al. |
| 5,587,172 | A | | 12/1996 | Cherukuri et al. |
| 5,622,716 | A | | 4/1997 | Barth |
| 5,622,717 | A | | 4/1997 | Fuisz |
| 5,654,003 | A | | 8/1997 | Fuisz et al. |
| 5,871,781 | A | | 2/1999 | Myers et al. |
| 5,925,682 | A | | 7/1999 | Gruber et al. |
| 6,596,298 | B2 | | 7/2003 | Leung et al. |
| 6,923,981 | B2 | | 8/2005 | Leung et al. |
| 7,025,983 | B2 | | 4/2006 | Leung et al. |
| 7,067,116 | B1 | | 6/2006 | Bess et al. |
| 9,877,921 | B2 | | 1/2018 | Rawas-Qalaji et al. |
| 2004/0247648 | A1 | | 12/2004 | Fadden et al. |
| 2005/0003467 | A1 | | 1/2005 | Hori |
| 2007/0202163 | A1 | * | 8/2007 | Rawas-Qalaji ........ A61K 9/006 424/464 |
| 2007/0202165 | A1 | | 8/2007 | Heuer et al. |

(Continued)

FOREIGN PATENT DOCUMENTS

| | | |
|---|---|---|
| CN | 101896204 A | 11/2010 |
| CN | 106109459 | 11/2016 |

(Continued)

OTHER PUBLICATIONS

Eisenburger et al, STIC Translation (Year: 1981).*

(Continued)

*Primary Examiner* — Jeffrey S Lundgren
*Assistant Examiner* — Ibrahim D Bori
(74) *Attorney, Agent, or Firm* — Cantor Colburn LLP

(57) ABSTRACT

The disclosure provides a method for systemic delivery of a therapeutically effective amount of epinephrine to a subject comprising orally administering dipivefrin or a dipivefrin salt to the subject. The disclosure also includes a method of treatment of a disease amenable to treatment by in vivo delivery of systemic epinephrine comprising administering dipivefrin or a dipivefrin salt to a subject in need of in vivo delivery of systemic epinephrine. The disease can be a respiratory disorder, anaphylaxis, cancer, or a microbial infection. The disclosure also includes dipivefrin or dipivefrin HCl orally dissolving tablets.

27 Claims, 9 Drawing Sheets

(56) References Cited

U.S. PATENT DOCUMENTS

| | | | |
|---|---|---|---|
| 2015/0005356 A1 | 1/2015 | Fleming | |
| 2015/0164827 A1* | 6/2015 | Rawas-Qalaji | A61K 31/137 514/653 |
| 2016/0220489 A1 | 8/2016 | Fleming et al. | |
| 2017/0020884 A1 | 1/2017 | Lichenstein et al. | |
| 2018/0147145 A1 | 5/2018 | Rawas-Qalaji et al. | |
| 2020/0276114 A1 | 9/2020 | Zhang | |

FOREIGN PATENT DOCUMENTS

| | | |
|---|---|---|
| CN | 106109459 A | 11/2016 |
| EP | 0159237 B1 | 5/1988 |
| EP | 2085071 A1 | 8/2009 |
| JP | 2004231557 A | 8/2004 |
| WO | 2007028247 A1 | 3/2007 |
| WO | 2007143676 A2 | 12/2007 |
| WO | 2017066787 A1 | 4/2017 |
| WO | 2018089570 A1 | 5/2018 |
| WO | 2019051387 A1 | 3/2019 |

OTHER PUBLICATIONS

Alaydi et al (Year: 2014).*
NSU Home (Year: 2013).*
Iso et al (Year: 1980).*
Rawas-Qalaji et al (Year: 2013).*
Alaydi, L. et al., "Development and Validation of RF-HPLC Method Using Photo Diode Array Detection for Simultaneous Quantification of Dipivefrin and Its Active Metabolites Co-eluting in Pharmaceutical Samples," Abstract CHM-05, Sixma Xi's 2014 International Research Conference, Nov. 7-9, 2014, Glendale, Arizona; 2 pages.
International Search Report; International Application No. PCT/US2018/050223; International Filing Date—Sep. 10, 2018; dated—Nov. 30, 2018; 6 pages.
Written Opinion; International Application No. PCT/US2018/050223; International Filing Date—Sep. 10, 2018 dated—Nov. 30, 2018; 7 pages.
Bobek et al., "A Clinically Relevant, Syngeneic Model of Spontaneous, Highly Metastatic B16 Mouse Melanoma," Anticancer Research; 2010, vol. 30, pp. 4799-4804.
Brown et al., "Cancer, Physical Activity, and Exercise," Compr Physiol.; Oct. 2012, vol. 2(4), pp. 2775-2809.
Dimitrov et al., "Selective Mobilization of Cytotoxic Leukocytes by Epinephrine," The Journal of Immunology, 2010; 184: pp. 503-511.
Dipivefrin Hydrochloride, www.drugs.com; May 1, 2018. pp. 1-10.
Formulation and Diffusion of Epinephrine's Prodrug for Anaphylaxis Treatment, NSU Home, Academic Affairs, 2013-2014 Winners, 3 pages.
Formulation and Diffusion of Epinephrine's Prodrug: https://www.nova.edu/academic-affairs/faculty-research-grant/winners1314/formulation-diffusion-epinephrines-prodrug.html, accessed Aug. 23, 2018.
Iso et al., "Antianaphylactic Effects of Dipivalyl Epinephrineand Related Compounds in Rat Conjunctiva," Invest. Ophthalmol. Vis. Sci.; Jul. 1980, vol. 19; pp. 824-826.
Iwasaki & Pillai, "Innate Immunity to Influenza Virus Infection," Nat. Rev. Immunol, Author Manuscript; available in PMC, Jul. 21, 2014, pp. 1-34.
Kox et al., "Voluntary Activation of the Sympathetic Nervous System and Attenuation of the Innate Immune Response in Humans," PNAS, May 20, 2014; vol. 111, No. 20, pp. 7379-7384.
Pedersen et al., "Voluntary Running Suppresses Tumor Growth through Epinephrine- and IL-6-Dependent NK Cell Mobilization and Redistribution," Mar. 8, 2016; Cell Metabolism 23, 1-9, Elsevier Inc.
Van Der Poll et al., "Epinephrine Inhibits Tumor Necrosis Factor-α and Potentiates Interleukin 10 Production During Human Endotoxemia," J Clin. Invest., vol. 97, No. 3, Feb. 1996, pp. 713-719.

Wood et al., "Safety of Epinephrine for Anaphylaxis in the Emergency Setting," World Journal of Emergency Medicine, 2013, vol. 4, No. 4, pp. 245-251.
Form PCT International Preliminary Examining Authority 408 received from the EPO dated Aug. 8, 2019.
Response to Written Opinion for PCT/US2018/050223, filed with the EPO dated Feb. 26, 2019.
Allen, "Rapid-Dissolve Technology," International Journal of Pharmaceutical Compounding, (2003),vol. 7, (No. 6), pp. 449-450.
Aurora et al., "Oral Disintegrating Technologies," Drug Delivery Technoloogy, (2005), vol. 5., (No. 3), pp. 50-54.
Buchwald et al., "Long-Term, Continuous Intravenous Heparin Administration by an Implantable Infusion Pump in Ambulatory Patients With Recurrent Venous Thrombosis," Surgery, (1980), vol. 88, (No. 4), pp. 507-516.
Chang et al., "Fast-Dissolving Tablets," Pharmaceutical Technology, (2000), (No. 24), pp. 53-58.
Dobetti, "Fast-Melting Tablets: Developments and Technologies," Pharmaceutical Technology Drug Delivery, Europe 12, (2001), pp. 44-50.
Ellman et al., "A New and Rapid Colorimetric Determination of Acetylcholinesterase Activity," Biochemical Pharmacology, Pergamon Press Ltd., (1961), vol. 7, pp. 88-95.
Goodson, "Dental Applications," Chapter 6, pp. 115-138, In "Medical Applications of Controlled Release, vol. 2, Applications and Evaluation," by RS Langer & DL Wise, eds, (1984), CRC Press.
Hamilton et al., "Orally Disintegrating Tablets, Advanced Orally Disintegratring Tablets Bring Significant Benefits to Patients and Product Life Cycles," Drug Delivery Technology, (2005), vol. 5, (No. 1), pp. 34-37.
Langer "New Methods of Drug Delivery," Science, (1990), vol. 249, pp. 1527-1533.
Nakamura et al., "Characterization of Esterases Involved in the Hydrolysis of Dipivefrin Hydrochloride," Ophthalmic Res., (1993), (No. 25), pp. 46-51.
Oropesa et al., "Characterization of Plasma Cholinesterase in Rabbit and Evaluation of the Inhibitory Potential of Diazinon," Ecotoxicology and Environmental Safety 100, (2014), pp. 39-43.
Parakh et al., "A Review of Mouth Dissolving Tablet Technologies," Pharmaceutical Technology, (2003), (No. 27), pp. 92-100.
Sastry et al., "Process Development and Scale-Up of Oral Fast-Dissolving Tablets," In Drug Delivery to the Oral Cavity, CRC Press, Boca Raton, (2005), pp. 311-316.
Sastry et al., "Recent Technological Advances in Oral Drug Delivery—A Review," Pharm Sci. Technology Today, (2000), vol. 3, (No. 4), pp. 138-145.
Saudek et al., "A Preliminary Trial of the Programmable Implantable Medication System for Insulin Delivery," The New England Journal of Medicine, (1989), vol. 321, (No. 9), pp. 574-579.
Second Written Opinion; Application No. PCT/US2018/050223; International Filing Date—Sep. 10, 2018; dated—Aug. 9, 2019, 5 pages.
Sefton, "Implantable Pumps," Crit. Rev. Biomed Eng., (1987), (No. 14) (3): 201-40,—Abstract Only.
Treat et al., "Liposome Encapsulated Doxorubicin Preliminary Results of Phase I and Phase II Trials," In "Liposomes in the Therapy of Infectious Diseases and Cancer," Alan R. Liss, Inc., (1989), pp. 353-365.
Verma et al., "Current Status of Drug Delivery Technologies and Future Directions," Pharmaceutical Technology On-Line, (2001), (No. 25)(2), pp. 1-14.
Anderson et al., "Site of Ocular Hydrolysis of a Prodrug, Dipivefrin, and a Comparison of its Ocular Metabolism with that of the Parent Compound, Epinephrine," Association for Res. in Vis. and Ophthal., Inc., (1980), vol. 19, (No. 7), pp. 817-823.
International Preliminary Report on Patentability; International Application No. PCT/US2018/050223; International Filing Date—Sep. 10, 2018; dated—Nov. 28, 2019; 6 pages.
Eisenburger et al., "Comparative Pharmacological Study on D, 1-Adrenaline Dipivalate Hydrochloride and 1-Adrenaline Hydrochloride After Local and Oral Administration," German Article, Klinge Pharma GmbH & Co., (2019), 37 pages.

(56) References Cited

OTHER PUBLICATIONS

Bahar et al. "Species Difference of Esterase Expression and Hydrolase Activity in Plasma," Journal of Pharmaceutical Sciences, (2012) vol. 101, (No. 10), pp. 3979-3988.

Introini-Collison, et al., "Memory-Enhancing Effects of Post-Training Dipivefrin and Epinephrine: Involvement of Peripheral and Central Adrenergic Receptors," Brain Research, No. 572, (1992); pp. 81-86.

Kemp, et al., "Epinephrine: The Drug of Choice for Anaphylaxis—A Statement of the World Allergy Organization," World Allergy Organization Journal, (2008) Supplement 2, pp. S18-S26.

Sicherer, S.C., et al., "Epinephrine for First-Aid Management of Anaphylaxis," American Academy of Pediatrics, (2017) vol. 139, (No. 3) pp. 1-11.

Simons, F.E., et al., "Can Epinephrine Inhalations Be Substituted for Epinephrine Injection in Children at Risk for Systemic Anaphylaxis?" American Academy of Pediatrics (2000), vol. 106, (No. 5); pp. 1040-1044.

Simons, K.J. et al., "Sublingual Epinephrine Administration in Humans: A Preliminary Study," J. of Allergy and Clin. Immunol., (Feb. 2004) 113, S260 Abstracts.

Jerzsele, "Comparative Veterinary Pharmacokinetics," In book: Readings in Advanced Pharmacokinetics—Theory, Methods and Applications, Apr. 20, 2011; pp. 179-198.

Written Opinion of Singapore Intellectual Property Office for Application No. 11202001397V; dated—Jan. 18, 2021; 5 pages.

Embase DN: 30435859, (2000), Abstract & Korean Journal of Dermatology, (2000), vol. 38, No. 5, pp. 635-642.

Shock, "Mapping Out Treatment of Anaphylactic Shock With Epinephrine," (2007) v. 22(2), pp. 70-75, In Japanese with English Abstract.

Menninger, "The Oral Administration of Epinephrine," (1927), Arch. Internal Medicine (Chic)l, vol. 40, No. (5); pp. 701-714.

\* cited by examiner

Bacterial counts in blood 4 hours post infection ($p < 0.05$, 2-tailed, unpaired t-test)

METHODS OF USING DIPIVEFRIN

CROSS REFERENCE TO RELATED APPLICATION

This application claims priority of U.S. provisional application No. 62/555,854, filed Sep. 8, 2017, which is hereby incorporated by reference in its entirety.

BACKGROUND

This disclosure relates to dipivefrin, a prodrug of epinephrine, and methods of treatment using dipivefrin to safely and rapidly deliver systemic epinephrine.

Epinephrine, also known as adrenaline, is a hormone and neurotransmitter naturally produced by both the adrenal glands and certain neurons. It is widely used, in injectable form, to treat anaphylaxis, a severe allergic reaction, asthma attacks, and to re-establish normal cardiac rhythm during cardiac arrest.

Injectable epinephrine has also been shown to be efficacious for preventing and treating cancer. U.S. Pat. No. 5,925,682 discloses that injecting a mammal with an effective amount of epinephrine results in the significant reduction of tumorous growth.

Regular exercise has also been shown to reduce the risk of a wide spectrum of types of cancer and cancer recurrence, including breast cancer, colon and rectal cancer, pancreatic cancer, prostate cancer, endometrial cancer, ovarian cancer, and lung cancer. One mechanism behind this protection may be due to the fact that exercise stimulates epinephrine secretion. Pedersen et al. (Cell Metabolism, 23, 1-9, Mar. 8, 2016) observed that exercise decreases tumor incidence and growth by over 60% across several mouse tumor models through a direct regulation of NK cell mobilization and trafficking in an epinephrine- and IL-6-dependent manner.

The biologic and pharmacologic effects of epinephrine are brought about by its binding to the alpha and beta adrenergic receptors. The distribution of adrenergic receptors on different cells accounts for the multitude of effects of epinephrine. Epinephrine binding to alpha receptors results in the dilation of blood vessels in skeletal muscles and the liver.

Epinephrine can cause increases in heart-rate and blood pressures. These effects are hazardous, and therefore limit the available use of epinephrine treatments.

The clinical dosage of intravenously administered epinephrine is usually much less than that given by intramuscular or subcutaneous injection. Also, the effects of intravenously injected epinephrine differ from the effects of subcutaneous injection or slow intravenous infusion of the compound. This is believed to be due to slow absorption of subcutaneous injected epinephrine due to the drug's local vasoconstrictor action. In fact, the effects of subcutaneously injected doses as large as 0.5 to 1.5 mg epinephrine can be duplicated by intravenous infusion of as little as 10-30 μg/min. Furthermore epinephrine cannot be administered orally.

Epinephrine taken orally is not well absorbed. All drugs taken orally enter the liver through the hepatic portal circulation before entering systemic circulation. The hepatic portal circulatory system is the venous drainage of the upper GI tract, carrying molecules absorbed by the gut into veins leading to the liver. Epinephrine is a catecholamine, a class of monoamine compounds that has a catechol and a side-chain amine Epinephrine is known to be inactivated by two enzymes—monoamine oxidase (MAO) and catechol-O-methyltransferase (COMT). MAO oxidizes the side-chain amine and COMT acts on the catechol part of epinephrine. MAO and COMT are present in the liver and the intestinal wall. Both enzymes are very active and quickly destroy orally administered epinephrine before it reaching systemic circulation.

Several needle-free approaches to deliver epinephrine systemically for anaphylaxis have been attempted, e.g. inhalation, sublingual, and intranasal routes. Epinephrine inhalation has been shown to be ineffective when used in children because the number of epinephrine inhalations required and the bad taste of inhaled epinephrine cause most children to be unable to inhale sufficient epinephrine to achieve the therapeutic concentration rapidly and significantly. A study in rabbits showed that epinephrine administered via a sublingual route can be systemically absorbed at the equivalent amount to IM epinephrine. However, the equivalent sublingual dose (40 mg) was about 100-fold higher than the usual IM dose (0.3 mg). The large dose is necessary for the sublingual route is probably due to its mucosal enzymatic degradation by COMT, as well as poor intrinsic mucosal transportation due to the strong vasoconstriction caused by epinephrine itself.

Intranasal delivery of epinephrine for anaphylaxis has been disclosed in US patent application US 2015/0005356 A1 and references cited therein. But to overcome the mucosal enzymatic degradation by COMT, as well as poor intrinsic mucosal transportation due to the strong vasoconstriction caused by epinephrine itself, a reversible catechol-O-methyl transferase (COMT) inhibitor and a vasodilator are required, which can cause serious side effects. A nasal spray with a high loading dose of epinephrine (5 mg) dissolved in normal saline free of a reversible catechol-O-methyl transferase (COMT) inhibitor and a vasodilator was given to normal human subjects and was compared with intramuscular epinephrine in a recent study by Srisawat C. et al. Asian Pac. J. Allergy Immunol. (2016) 34:38-43. The study revealed a peak plasma concentration ($T_{max}$) reached in 70±17 minutes. A $T_{max}$ of 70±17 minutes even at the higher loading dose of epinephrine, is insufficient to be of any utility in anaphylactic shock. Paradoxically, the data on the PK of the 1M epinephrine injection with a $T_{max}$ of 67±43 minutes is also unacceptable.

There remains a need in the art for methods of delivering epinephrine systemically that are safer and more convenient than the current injectable epinephrine formulations for treatment of various diseases such as anaphylaxis There is also a need for a method of delivering epinephrine that provides low systemic absorption, to reduce the occurrence of side effects.

SUMMARY

Dipivefrin is a dipivaloyl ester prodrug of epinephrine. Dipivefrin hydrochloride has been approved for ocular use as a 0.1% ophthalmic solution indicated as initial therapy for the control of intraocular pressure in chronic open-angle glaucoma. Dipivefrin is biotransformed into epinephrine at the site of administration (the eye) by enzymatic hydrolysis with low systemic epinephrine absorption.

The inventor has surprisingly discovered that dipivefrin can safely and effectively deliver epinephrine to the systemic circulation when taken orally.

Disclosed is a method for systemic delivery of epinephrine to a subject, comprising orally administering a dipivefrin composition to a subject.

A method for treating anaphylaxis comprises orally administering a dipivefrin composition to a subject experiencing anaphylaxis.

A method for treating cancer comprises administering a dipivefrin composition to a subject in need of treatment of a cancer.

A method for treating a microbial infection comprises administering a dipivefrin composition to a subject in need of treatment of a microbial infection.

The above described and other features are exemplified by the following figures and detailed description.

BRIEF DESCRIPTION OF THE DRAWINGS

The following is a brief description of the drawings which are presented for the purposes of illustrating the exemplary embodiments disclosed herein and not for the purposes of limiting the same.

DETAILED DESCRIPTION

Figure 1:
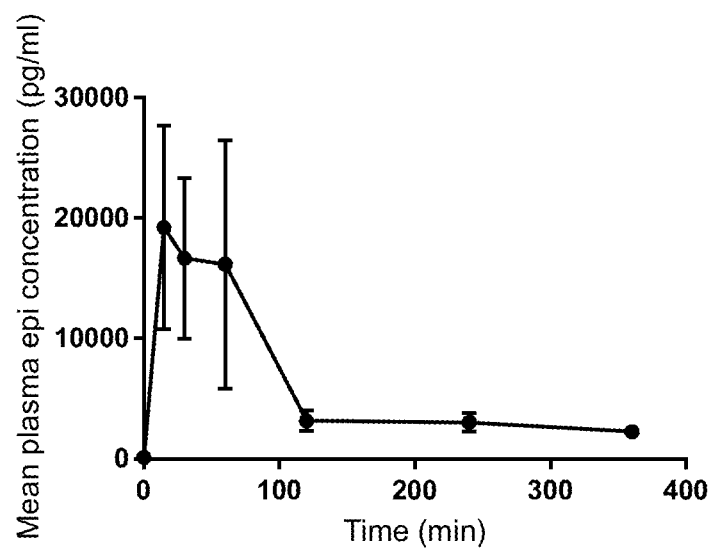
FIG. 1 is a graph of mean plasma epinephrine (epi) concentration as a function of time in mice (N=3) after oral administration of 21.2 mg/kg dipivefrin hydrochloride (19.2 mg/kg freebase; equivalent to 10 mg/kg racemic epinephrine).

Administration of dipivefrin has been found to be effective for the safe and rapid systemic delivery of epinephrine to a subject. Administration of dipivefrin can be by any appropriate route, for example oral administration or injection. Various diseases are amenable to treatment with systemic epinephrine, such as anaphylaxis, cancer, and microbial infections, however safe and convenient means of dosing epinephrine to individuals has been problematic. In particular, epinephrine has been limited to administration by injections for lack of oral absorption, a route which is less convenient than oral dosing.

The inventor has surprisingly discovered that dipivefrin can safely and effectively deliver epinephrine to the systemic circulation when taken orally. This result was not expected because first, although unlike epinephrine, dipivefrin does not possess a free catechol group making it an unlikely substrate of catechol-O-methyltransferase (COMT), conversion to epinephrine via ester hydrolysis while transitioning the GI tract and subsequent degradation of the resulting epinephrine by COMT was still expected. Second, dipivefrin has the same amine side-chain functional group as epinephrine, which could be inactivated by the same monoamine oxidase (MAO) present in both the GI tract and liver that is responsible for oral epinephrine inactivation. Thirdly, even if dipivefrin reaches the systemic circulation after oral administration, there is no guarantee it would be biotransformed into epinephrine in a manner sufficiently timely and efficient for it to be effective as a therapeutic agent. Biotransformation of prodrugs in vivo requires presence of appropriate enzymes that are often species specific and tissue specific. Therefore, the inventor was surprised to discover that dipivefrin can safely and effectively deliver epinephrine to the systemic circulation when administered orally.

Surprisingly, administration of dipivefrin, even oral administration, is shown to be effective for the safe and rapid systemic delivery of epinephrine to a subject and for treatment of anaphylaxis, cancer, and microbial infection.

The present disclosure provides compositions and methods related to the use of dipivefrin for treating anaphylaxis, cancer, or a microbial infection in a subject, preferably a human subject, in need of such treatment. In addition, the present disclosure provides novel therapeutic approaches to treating anaphylaxis, cancer, or a microbial infection based upon therapeutic regimens utilizing dipivefrin alone, as a monotherapy, or in combination with at least one additional therapeutic agent, such as an anticancer agent or an antimicrobial agent.

In one aspect, the present disclosure provides a method for treating anaphylaxis, cancer, or a microbial infection, the method comprising administering to a subject in need thereof a dipivefrin composition comprising dipivefrin, or a pharmaceutically acceptable salt, solvate, clathrate, hydrate, polymorph, prodrug, analog or derivative thereof. In one embodiment, the dipivefrin composition comprises dipivefrin freebase or dipivefrin hydrochloride.

Terminology

As used herein, the term "dipivefrin composition" refers to a composition comprising dipivefrin (freebase), or may encompass pharmaceutically acceptable salts, solvates, clathrates, polymorphs, analogs or derivatives of dipivefrin, as described below. A preferred dipivefrin composition comprises dipivefrin or dipivefrin hydrochloride.

The structure of dipivefrin is shown in Formula (I).

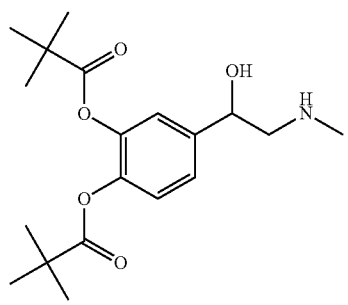

(I)

The IUPAC name of dipivefrin is 4-(1-hydroxy-2-(methylamino)ethyl)-1,2-phenylene bis(2,2-dimethylpropanoate). The synonyms of dipivefrin are [±]-3,4-Dihydroxy-α-[(methylamino)methyl]benzyl alcohol 3,4-dipivalate, 1-(3',4'-Dipivaloyloxyphenyl)-2-methylamino-1-ethanol, 4-[1-Hydroxy-2-(methylamino)ethyl]-O-phenylene divavalate, Dipivalyl Epinephrine, and [2-(2,2-Dimethylpropanoyloxy)-4-[1-hydroxy-2-(methylamino)ethyl]phenyl]2,2-dimethylpropanoate. Dipivefrin has CAS Reg. No. 52365-63-6. Dipivefrin hydrochloride has CAS Reg. No. 64019-93-8.

Dipivefrin and the pharmaceutically acceptable salts thereof can be prepared, for example, according to the methods described in U.S. Pat. No. 3,809,714, which is hereby incorporated by reference for its teachings regarding dipivefrin synthesis.

As used herein, the term "pharmaceutically acceptable salt" is a salt formed from, for example, an acid and a basic group of a dipivefrin composition. Illustrative salts include, but are not limited to, sulfate, citrate, acetate, oxalate, chloride, acid chloride, bromide, iodide, nitrate, phosphate, acid phosphate, isonicotinate, lactate, salicylate, acid citrate, tartrate, oleate, tannate, pantothenate, bitartrate, ascorbate, succinate, maleate, besylate, gentisinante, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts. In an embodiment, the salt of dipivefrin is a hydrochloride salt. Unless clearly contraindicated by the context, "dipivefrin" includes the pharmaceutically acceptable salts of dipivefrin.

The term "pharmaceutically acceptable salt" also refers to a salt prepared from a composition having an acidic functional group, such as a carboxylic acid functional group, and a pharmaceutical acceptable inorganic or organic base.

The term "pharmaceutically acceptable salt" also refers to a salt prepared from a composition having a basic functional group, such as an amino functional group, and a pharmaceutically acceptable inorganic or organic acid.

An "active agent" means a compound (including for example, dipivefrin), element, or mixture that when administered to a subject, alone or in combination with another compound, element, or mixture, confers, directly or indirectly, a physiological effect on the subject. The indirect physiological effect may occur via a metabolite or other indirect mechanism.

The terms "administer", "administering", "administered" or "administration" refer to any manner of providing an active agent (such as dipivefrin or a pharmaceutically acceptable salt thereof) to a subject or patient. Routes of administration can be accomplished through any means known by those skilled in the art. Such means include oral, buccal, intravenous, subcutaneous, intramuscular, transdermal, and inhalation, sublingual, intranasal. Oral administration is a preferred route of dipivefrin administration.

The terms "taken orally" and "oral administration" refer to a manner of providing an active agent to a subject or patient by the mouth through the gastrointestinal tract (digestive tract, digestional tract, GI tract, GIT, gut, or alimentary canal) and are used interchangeably. The gastrointestinal tract is an organ system within humans and other animals which takes in food, digests it to extract and absorb energy and nutrients, and expels the remaining waste as feces. The mouth, esophagus, stomach and intestines are part of the gastrointestinal tract.

A "dosage form" means a unit of administration of an active agent. Examples of dosage forms include tablets, capsules, oral thin films, orally dissolving (or disintegrating) dosage forms, sprinkles, injections, suspensions, liquids, emulsions, creams, ointments, suppositories, inhalable forms, transdermal forms, intranasal spray and the like.

An "orally dissolving (or disintegrating) dosage form" is a solid dosage form that disintegrates or dissolves rapidly, usually within a matter of seconds, when placed in the mouth. Orally dissolving dosage forms are designed to disintegrate or dissolve rapidly on contact with saliva, thus eliminating the need for chewing, swallowing, or taking the solid dosage with water. An orally dissolving dosage can promote pregastric absorption of the active ingredients through buccal, sublingual, oropharyngeal and esophageal membranes. As a result, an orally dissolving dosage can provide faster onset of action and higher bioavailability than a conventional solid dosage form.

"Pharmaceutical compositions" are compositions comprising at least one active agent, e.g., dipivefrin, and at least one other substance, such as a carrier, excipient, or diluent. Pharmaceutical compositions meet the U.S. FDA's GMP (good manufacturing practice) standards for human or non-human drugs.

The term "carrier" applied to pharmaceutical compositions described herein refers to a diluent, excipient, or vehicle with which an active compound is provided.

A "pharmaceutically acceptable excipient" means an excipient that is useful in preparing a pharmaceutical composition that is generally safe, non-toxic, and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient. The patient may also be a livestock animal (e.g., sheep, pigs, horses, cows) or a companion animal (dog, cat).

The term "subject" includes any human or non-human animal. For example, the methods and compositions disclosed herein can be used to deliver systemic epinephrine to a subject in need thereof. In a particular embodiment, the subject is a human. The subject may also be a livestock animal (e.g., sheep, pigs, horses, cows) or a companion animal (dog, cat).

A "therapeutically effective amount" or "effective amount" is that amount of a pharmaceutical agent to achieve a pharmacological effect. The term "therapeutically effective amount" includes, for example, a prophylactically effective amount, that is an amount effective to significantly reduce the probability of occurrence of a disorder in a patient at risk for the disorder. An "effective amount" of dipivefrin is an amount needed to achieve a desired pharmacologic effect or therapeutic improvement without undue adverse side effects. The effective amount of dipivefrin will be selected by those skilled in the art depending on the particular patient and the type of conditions being treated. It is understood that "an effective amount" or "a therapeutically effective amount" can vary from patient to patient, due to variation in general condition of the subject, the condition being treated, the severity of the condition being treated, and the judgment of the prescribing physician. When discussing a method of treating cancerous tissue, an effective amount includes an amount effective to have a statistically significant and favorable effect on the rate of the patient's cancer proliferation over time or on a level of biological marker for the cancer.

The terms "treating" and "treatment" mean implementation of therapy with the intention of reducing in severity or frequency symptoms, elimination of symptoms or underlying cause, prevention of the occurrence of symptoms or their underlying cause, or the improvement or remediation of damage due to a disorder or disease. In certain embodiments "treatment" includes prophylactic treatment, which is administering an amount of dipivefrin effective to significantly reduce the proliferation of cancerous tissue or reduce the chance of infection by a microbial pathogen a patient. In certain embodiments treatment includes inhibiting the onset of anaphylaxis or reducing the severity of allergy symptoms in a subject exposed to an allergen.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Dipivefrin is a prodrug of epinephrine, a compound having structure (II) below.

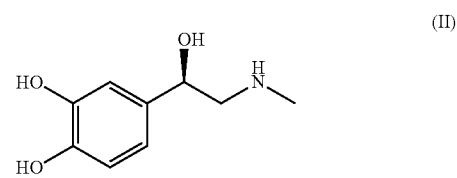

L-epinephrine has the CAS Reg. No. 51-43-4.

Disclosed herein is a method for systemic delivery of epinephrine to a subject, comprising orally administering a dipivefrin composition to a subject.

Also disclosed herein is a method of treatment of a disease amenable to treatment by in vivo delivery of systemic epinephrine to a subject in need thereof. The method comprises administering a dipivefrin composition to a subject in need of in vivo delivery of systemic epinephrine. Non-limiting examples of such diseases include an allergic reaction, anaphylaxis, cancer, and microbial infections. Administration of dipivefrin can be performed by any suitable route, including oral, buccal, intravenous, subcutaneous, intramuscular, topical, transdermal, sublingual, intranasal and inhalation. Dipivefrin is administered in a therapeutically effective amount. The dipivefrin can be administered as a pharmaceutical composition containing dipivefrin. In certain embodiments administration is oral administration and the dipivefrin is administered as an oral dosage form such as an oral solution or suspension, a tablet (e.g. an orally dissolving/disintegrating tablet), a capsule, a sprinkle, or a powder.

Methods for Treating Anaphylaxis

The method can be a method for treating anaphylaxis. The method can comprise administering a therapeutically effective amount of dipivefrin to a subject experiencing anaphylaxis. The method also comprises administering a therapeutically effective amount of dipivefrin to a subject experiencing a less severe allergic reaction. In preferred embodiments, a dipivefrin composition is administered orally, for example in an oral tablet, capsule, solution, suspension, or orally dissolving film. In one embodiment, the dipivefrin composition comprises dipivefrin freebase or dipivefrin hydrochloride. The dipivefrin composition can be administered in an amount sufficient to provide a therapeutically effective plasma level of epinephrine in the subject. For example an amount of dipivefrin sufficient to provide an epinephrine plasma level of 0.1 to 50 ng/mL In one embodiment, the oral tablet is an orally dissolving tablet or orally disintegrating tablet (ODT). An ODT is a solid dosage form containing medicinal substances which dissolves or disintegrates rapidly, usually within a matter of seconds, when placed upon the tongue. Characteristics that are exhibited by ODTs include low tablet weight, small tablet size, highly soluble components, and rapid dissolution or disintegration.

In one embodiment, the oral tablet is a fast dissolving sublingual tablet. In certain embodiments the oral tablet is not a sublingual tablet.

The method can comprise administering to the subject a therapeutically effective amount of a dipivefrin composition less than 1 min, less than 2 min, less than 5 min, less than 10 min, less than 20 min, or less than 30 min after the onset of anaphylaxis.

The method can comprise administering to the subject a therapeutically effective amount of a dipivefrin composition 6 hours before, 5 hours before, 4 hours before, 3 hours before, 2 hours before, 1 hour before, 30 min before, 10 min before, or 5 min before a potential exposure to an anaphylaxis trigger for the subject.

An "anaphylaxis trigger" means a substance that causes an anaphylactic reaction in the subject. Examples of anaphylaxis triggers include food, such as peanuts, tree nuts, fish, milk; certain medications, such as antibiotics (penicillins and cephalosporins) and analgesics (aspirin, ibuprofen); venom from insects, including bees, yellow jackets, wasps, hornets, and fire ants; and latex from natural rubber.

Methods for Treating Cancer

The method can be a method for treating cancer comprising administering a dipivefrin composition to a subject in need of treatment of a cancer. The cancer can be, for example, a brain cancer, a glioma, a sarcoma, a skin cancer, a breast cancer, a lung cancer, a non-small-cell lung cancer, a mesothelioma, an appendicular cancer, a genitourinary cancer, a renal cell carcinoma, a prostate cancer, a bladder cancer, a testicular cancer, a penile cancer, a cervical cancer, an ovarian cancer, a von Hippel Lindau disease, a head and neck cancer, a gastrointestinal cancer, a hepatocellular carcinoma, a gallbladder cancer, an esophageal cancer, a gastric cancer, a colorectal cancer, a pancreatic cancer, a neuroendocrine tumor, a thyroid tumor, a pituitary tumor, an adrenal tumor, a hematological malignancy, a lymphoma, a leukemia, or a combination thereof. The skin cancer can be a melanoma, a basal cell cancer, or a squamous cell skin carcinoma.

In one embodiment, the cancer is renal cell carcinoma.

In one embodiment, the cancer is breast cancer.

In one embodiment, the cancer is acute myeloid leukemia (AML) or acute lymphoblastic leukemia (ALL).

In one embodiment, the cancer is a B-cell lymphoma.

In one embodiment, the cancer is a non-Hodgkin's B-cell lymphoma.

In one embodiment, the cancer is a glioma.

The method for treating cancer can be a combination therapy. As used herein, "combination therapy" includes administration of a dipivefrin composition with at least one anticancer treatment in addition to dipivefrin, as part of a specific treatment regimen intended to provide a beneficial effect from the co-action of the dipivefrin composition and the additional anticancer treatment.

Thus, the method for treating cancer can comprise administering dipivefrin and at least one additional anticancer treatment to a subject in need thereof. The additional anticancer treatment can be surgery, chemotherapy, radiation, endocrine therapy, transplantation of stem cells, a molecularly-targeted therapy, or a biological therapy. Examples of chemotherapeutics include anthracyclines such as doxorubicin and daunoribicin, taxanes such as paclitaxel and docetaxel, and platinum-based chemotherapies such as cisplatin and oxaliplatin. Examples of an endocrine therapy include tamoxifen, aromatase inhibitors, and androgen deprivation therapy for prostate cancer. Examples of a molecularly-targeted therapy include hormone therapies, signal transduction inhibitors, gene expression modulators, apoptosis inducers, angiogenesis inhibitors, immunotherapies, monoclonal antibodies that deliver toxic molecules, cancer vaccines, and gene therapy. Examples of biological therapy include monoclonal antibodies, or MAbs, cytokines, cancer treatment vaccines, *bacillus* Calmette-Guérin therapy (BCG), oncolytic virus therapy, gene therapy, and adoptive T-cell transfer therapy.

In one embodiment, the at least one additional anticancer treatment can be an immunotherapy that uses certain parts of a person's immune system to fight diseases such as cancer. Examples of an immunotherapy include monoclonal antibodies, immune checkpoint inhibitors, cancer vaccines, cytokines and immunomodulating drugs (or IMiDs), Bacille Calmette-Guérin (BCG), imiquimod, and combinations thereof. Examples of the adoptive cell transfer (ACT) therapy include a CAR (chimeric antigen receptor) modified T-cell therapy such as tisagenlecleucel and CAR modified NK cell therapy.

In one embodiment, the cancer vaccine is sipuleucel-T, approved for prostate cancer in the United States.

The present disclosure also provides methods comprising a combination therapy.

In one embodiment, the method further comprises administering at least one additional active agent to the subject. The at least one additional active agent may be a therapeutic agent or a non-therapeutic agent. The at least one additional active agent may be administered in a single dosage form with the dipivefrin composition, or in a separate dosage form from the dipivefrin composition. In one embodiment, the at least one additional active agent is selected from the group consisting of an alkylating agent, an intercalating agent a tubulin binding agent, a corticosteroid, and combinations thereof.

The at least one additional active agent may be a therapeutic agent, for example an anti-cancer agent or a cancer chemotherapeutic agent, a non-therapeutic agent, or combinations thereof. With respect to therapeutic agents, the beneficial effect of the combination includes, but is not limited to, pharmacokinetic or pharmacodynamics co-action resulting from the combination of therapeutically active compounds. With respect to non-therapeutic agents, the beneficial effect of the combination may relate to the mitigation of toxicity, a side effect, or an adverse event associated with a therapeutically active agent in the combination.

In one embodiment, the at least one additional active agent is a therapeutic agent. In one embodiment, the therapeutic agent is an anti-cancer agent. In one embodiment, the anticancer agent is a Bruton's tyrosine kinase (BTK) inhibitor such as ibrutinib. In one embodiment, a dipivefrin composition is administered along with ibrutinib in a single dosage form or in separate dosage forms. In one embodiment, the dosage form is an oral dosage form. In another embodiment, the dosage form is suitable for intravenous administration.

In one embodiment, the anti-cancer agent is a drug that is approved for use in treating lymphoma. Non-limiting examples of such drugs include belinostat (Beleodaq), bendamustine hydrochloride, bleomycin (e.g. Blenoxane), bortezomib (Velcade), brentuximab vedotin (e.g. Adcetris), carmustine (e.g. Becenum, BiCNU, Carmubris), chlorambucil (e.g. Leukeran, Linfolizin), cyclophosphamide (e.g. Amboclorin, Clafen, Cytoxan, Neosar), denileukin diftitox (Ontak), doxorubicin hydrochloride, ibritumomab tiuxetan (e.g. Zevalin), ibrutinib (e.g. Imbruvica), idelalisib (e.g. Zydelig), intron A (recombinant interferon Alfa-2b), romidepsin (e.g. Istodax), lenalidomide (e.g. Revlimid), liposomal cytarabine (e.g. DepoCyt), mechlorethamine hydrochloride, methotrexate (Abitrexate, Folex, Methotrexate LPF, Mexate-AQ) mechlorethamine hydrochloride, (e.g. Mustargen), nelarabine (e.g. Arranon), perixafor (e.g. Mozobil), pralatrexate (e.g. Folotyn), prednisone, rituximab (e.g. Rituxan), tositumomab and iodine I 131 tositumomab (e.g. Bexxar), vinblastine sulfate (e.g. Velban, Velsar), vincasar PFS vincristine sulfate (e.g. Vincasar PFS), and vorinostat (e.g. Zolinza).

In one embodiment, the anti-cancer agent is selected from an inhibitor of EZH2, e.g., EPZ-6438. In one embodiment, the anti-cancer agent is selected from taxol, vincristine, doxorubicin, temsirolimus, carboplatin, ofatumumab, rituximab, and combinations thereof.

In one embodiment, the at least one additional active agent is a B cell receptor pathway inhibitor. In some embodiments, the B cell receptor pathway inhibitor is a CD79A inhibitor, a CD79B inhibitor, a CD 19 inhibitor, a Lyn inhibitor, a Syk inhibitor, a PI3K inhibitor, a Blnk inhibitor, a PLCy inhibitor, a PKCP inhibitor, or a combination thereof. In some embodiments, the at least one additional active agent is an antibody, B cell receptor signaling inhibitor, a PI3K inhibitor, an IAP inhibitor, an mTOR inhibitor, a radioimmunotherapeutic, a DNA damaging agent, a proteasome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

In one embodiment, the at least one additional active agent is an inhibitor of the checkpoint signaling pathway involving the programmed death 1 (PD-1) receptor and its ligands (PD-L1/2). In one embodiment, the method comprises a combination of an anti-PD-L 1 agent and an anti-PD-1 agent. In one embodiment, the inhibitor is an anti-PD-L 1 agent selected from BMS-936559/MDx-1105 (a fully human, high affinity, immunoglobulin (Ig) G4 monoclonal antibody to PD-L1), MPDL3280A (an engineered human monoclonal antibody targeting PD-L 1), MSB0010718C and MEDI473. In one embodiment, the inhibitor is an anti-PD-1 agent selected from CT-011/pidilizumab, BMS-936558/MDX-1106/nivolumab, and pembrolizumab. In one embodiment, the inhibitor is selected from BMS-936559/MDX-1105, MPDL3280A, MSB0010718C, MEDI473, CT-011/pidilizumab BMS-936558/MDX-1106/nivolumab, and pembrolizumab, and combinations of two or more of any of the foregoing. In one embodiment, the inhibitor is selected from the group consisting ipilimumab, pembrolizumab, nivolumab, atezolizumab, avelumab, durvalumab and combinations thereof. In one embodiment, the inhibitor is an anti-CTLA-4 antibody. An example of anti-CTLA-4 antibody is Ipifirtmmab (trade name Yervoy).

In one embodiment, the at least one additional active agent is a therapeutic agent selected from the group consisting immunomodulatory drugs (IMids) capable of stimulating both NK cells and T-cells such as thalidomide, lenalidomide, and pomalidomide. In one embodiment, the combination therapy also includes an anti-inhibitory KIR antibody (IPH-2102).

In one embodiment, the at least one additional active agent is a therapeutic agent selected from inhibitors of indoleamine-2,3-dioxygenase (IDO). In one embodiment, the inhibitor is selected from the group consisting indoximod, INCB024360, NLG 919, IDO1-derived peptide, epacadostat, GDC0919 or a combination thereof.

In one embodiment, the at least one additional active agent is a therapeutic agent selected from the group consisting of ibrutinib, rituximab, doxorubicin, prednisolone, vincristine, velcade, and everolimus, and combinations thereof. In one embodiment, the at least one additional active agent is a therapeutic agent selected from cyclophosphamide, hydroxydaunorubicin (also referred to as doxorubicin or Adriamycin™), vincristine (also referred to as Oncovin™), prednisone, prednisolone, and combinations thereof. In one embodiment, the at least one additional active agent is a therapeutic agent selected from the group consisting of BMS-936559/MDX-1105, MPDL3280A, MSB0010718C, MEDI473, CT-011/pidilizumab, BMS-936558/MDX-1106/nivolumab, and pembrolizumab, and combinations of two or more of any of the foregoing.

In one embodiment, the at least one additional agent is selected from chlorambucil, ifosphamide, doxorubicin, mesalazine, thalidomide, lenlidomide, temsirolimus, everolimus, fludarabine, fostamatinib, paclitaxel, docetaxel, ofattumumab, rituximab, dexamethasone, prednisone, CAL-101, ibritumomab, tositumomab, bortezomib, pentostatin, endostatin, or a combination thereof.

In one embodiment, the at least one additional active agent is a monoclonal antibody such as, for example, alemtuzumab, bevacizumab, catumaxomab, cetuximab, edrecolomab, gemtuzumab, ofatumumab, panitumumab, rituximab, trastuzumab, eculizumab, efalizumab, muromab-CB3, natalizumab, adalimumab, afelimomab, certolizumab pegol, golimumab, infliximab, basiliximab, canakinumab, daclizumab, mepolizumab, tocilizumab, ustekinumab, ibritumomab tiuxetan, tositumoma, abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, and zalutumumab, rituximab, certuximab, daraumumab, ublituximab (TG-1101), ocaratuzumab (AME-133), obinutuzumab (GA-101).

In one embodiment, the at least one additional active agent is a cytokine selected from the group consisting interferons (INFs) and interleukins (ILs). Examples of interferons include INF-alfa. Examples of interleukins include IL-2 (aldesleukin), IL-6, IL-12, IL-15, and IL-21.

In the context of combination therapy, administration of the dipivefrin composition may be simultaneous with, or sequential to, the administration of the one or more additional active agents. In another embodiment, administration of the different components of a combination therapy may be at different frequencies. The one or more additional active agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present disclosure.

The one or more additional active agents can be formulated for co-administration with a dipivefrin composition in a single dosage form, as described in greater detail herein. The one or more additional active agents can be administered separately from the dosage form that comprises the compound of the present disclosure. When the additional active agent is administered separately from the dipivefrin composition, it can be by the same or a different route of administration as the dipivefrin composition.

Preferably, the administration of a dipivefrin composition in combination with one or more additional active agents provides a synergistic response in the subject being treated. In this context, the term "synergistic" refers to the efficacy of the combination being more effective than the additive effects of either single therapy alone. The synergistic effect of a combination therapy according to the disclosure can permit the use of lower doses and/or less frequent administration of at least one active agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

In one embodiment, the dosage form of the dipivefrin composition is an oral dosage form. In another embodiment, the dosage form of the dipivefrin composition is suitable for intravenous administration. In one embodiment, where the dosage form is suitable for intravenous administration, administration is by a single injection or by a drip bag.

In one embodiment, the standard chemotherapy regimen comprises one or more therapeutic agents selected from the group consisting of ibrutinib, rituximab, doxorubicin, prednisolone, vincristine, velcade, cyclophosphoamide, dexamethasone and everolimus. In one embodiment, the standard chemotherapy regimen is selected from CHOP, (cyclophosphamide, hydroxydaunorubicin, Oncovin™ (vincristine), and prednisone or prednisolone), COOP (cyclophosamide, vincristine sulfate, prednisone), EPOCH (etoposide, prednisone, vincristine sulfate, cyclophosphamide, doxorubicin hydrochloride, Hyper-CVAD (cyclophosphamide, vincristine sulfate, doxorubicin hydrochloride, dexamethasone), ICE (ifosfamide, carboplatin, etoposide), R-CHOP (rituximab, cyclophosamide, vincristine sulfate, procarbazine hydrochloride, prednisone, and R-CVP (rituximab, cyclophosamide, vincristine sulfate, prednisone).

In one embodiment, the method is a method of treating a lymphoma using a combination therapy comprising a dipivefrin composition and a chemotherapy regimen for the treatment of the lymphoma. In one embodiment, the chemotherapy regimen is the CHOP regimen. In another embodiment, the chemotherapy regimen is selected from COOP, CVP, EPOCH, Hyper-CVAD, ICE, R-CHOP, and R-CVP.

"Combination therapy" also embraces the administration of the compounds of the present disclosure in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

The non-drug treatment can be selected from chemotherapy, radiation therapy, hormonal therapy, anti-estrogen therapy, gene therapy, and surgery. For example, a non-drug therapy is the removal of an ovary (e.g., to reduce the level of estrogen in the body), thoracentesis (e.g., to remove fluid from the chest), paracentesis (e.g., to remove fluid from the abdomen), surgery to remove or shrink angiomyolipomas, lung transplantation (and optionally with an antibiotic to prevent infection due to transplantation), or oxygen therapy (e.g., through a nasal cannula containing two small plastic tubes or prongs that are placed in both nostrils, through a face mask that fits over the nose and mouth, or through a small tube inserted into the windpipe through the front of the neck, also called transtracheal oxygen therapy).

Methods for Treating Microbial Infection

Provided in this disclosure is a method for treating a microbial infection comprising administering a dipivefrin composition to a subject in need of treatment of a microbial infection. The microbial infection can be a bacterial, viral, fungal, or parasitic infection.

The bacterial infection can be a mycobacterial infection; a Gram positive bacterial infection, such as a Spirochete infection, a *Staphylococcus* infection, a *Streptococcus* infection, a *Clostridium* infection, a *Vibrio* infection, a *Bacillus* infection, a *Salmonella* infection, a *Listeria* infection, or a *Corynebacterium* infection; or a Gram negative bacterial infection, such as an *E. coli* infection, a *Klebsiella pneumoniae* infection, an *Acinetobacter baumannii* infection, a *Pseudomonas aeruginosa* infection, a *Neisseria gonorrhoeae* infection, or a *Yersinia pestis* infection; a *Neisseria meningitides* infection; a *Hemophilus influenzae* B infection; a Lyme disease spirochetes infection; a *Mycobacterium leprae* infection; a *Pneumococcus* spp infection; a *Treponema pallidum* infection; a *Legionella pneumophilia* infection; a *Brucella abortus* infection, a *Mycobacterium tuberculosis* infection; a *Mycoplasma* infection; a *Bacillus anthracis* infection; a *Streptococcus agalactiae* infection; a *Streptococcus pyogenes* infection; a *Escherichia coli* infection; a *Neisseria gonorrhoeae* infection; a *Neisseria meningitides* infection; or a *Pseudomonas aeruginosa* infection.

The viral infection can include influenza, a herpes virus infection, a dengue virus infection, a human immunodeficiency virus infection, a hepatitis virus infection, a west Nile virus infection, a cytomegalovirus infection, a rabies virus infection, a flavivirus infection, a rhinovirus infection, a papillomavirus infection, a paramyxovirus infection, a parainfluenza virus infection, a retrovirus infection, or an infection caused by the following virus: Sendai virus, feline leukemia virus, Reo virus, polio virus, human serum parvo-like virus, simian virus 40, respiratory syncytial virus, mouse mammary tumor virus, Varicella-Zoster virus, dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, or blue tongue virus.

The fungal infection can be a yeast infection or an infection by a filamentous fungus. Examples of a fungal infection include systemic candidiasis, aspergillosis, cryptococcosis, blastomycosis, coccidioidomycosis, histoplasmosis, and mucormycosis, *Microsporum, Trichophyton, Epidermophyton, Sporothrix schenckii, Cryptococcus neoformans, Coccidioides immitis, Histoplasma capsulatum, Blastomyces dermatitidis,* or *Candida albicans.*

The parasitic infection can include malaria and an endoparasiticidal infection from helminths or filarial nematodes, *acanthamoeba* infection, *acanthamoeba keratitis* infection, African sleeping sickness, alveolar echinococcosis, amebiasis, American trypanosomiasis, ancylostomiasis, angiostrongyliasis, anisakiasis, ascariasis, babesiosis, balantidiasis, balamuthia, baylisascariasis, bed bugs, bilharzia, *Blastocystis hominis* infection, body lice infestation, capillariasis, cercarial dermatitis, Chagas disease, *Chilomastix mesnili* infection, clonorchiasis, CLM, "Crabs," cryptosporidiosis, cutaneous lava migrans, cyclosporiasis, cysticercosis, cystoisospora infection, *Dientamoeba fragilis* infection, diphyllobothriasis, *Dipylidium caninum* infection, dirofilariasis (*Dirofilaria* infection), DPDx, dracunculiasis, dog tapeworm, echinococcosis, elephantiasis, *Entamoeba histolytica* infection, *Entamoeba polecki*, enterobiasis, fascioliasis, fasciolopsiasis, filariasis, giardiasis, gnathostomiasis, guinea worm disease, head lice infestation, heterophyiasis, hookworm infection, hydatid disease, hymenolepiasis, intestinal roundworms, *Iodamoeba buetschlii* infection, *Isospora* infection, kala-azar, keratitis, leishmaniasis, loiasis, lymphatic filariasis, malaria, microsporidiosis, mite infestation, myiasis, *Naegleria* infection, neurocysticercosis, neglected parasitic infections in the U. S., neglected tropical disease, ocular larva migrans, onchocerciasis, opisthorchiasis, paragonimiasis, pediculosis, pthiriasis, pinworm infection, *Plasmodium* infection, *Pneumocystis jirovecii* pneumonia, *Pseudoterranova* infection, pubic lice infestation, raccoon roundworm infection, river blindness, Sappinia infection, sarcocystosis, scabies, schistosomiasis, sleeping sickness, soil-transmitted helminths, strongyloidiasis, swimmer's itch, taeniasis, tapeworm infection, toxocariasis, trichinellosis, trichinosis, trichomoniasis, trichuriasis, trypanosomiasis, visceral larva migrans, waterborne disease, whipworm infection, zoonotic disease, or zoonotic hookworm infection.

The method for treating microbial infection can further be a combination therapy comprising administering dipivefrin and at least one or more additional chemotherapy treatment that exerts direct inhibitory effect against the microbial pathogen to the subject, herein referred to as an "antimicrobial agent" The antimicrobial agent can be an antibiotic, an antifungal agent, an antiviral agent, an antiparasitic agent, or a combination thereof.

Examples of antibiotics include a beta-lactam antibiotic, a tetracycline, a sulfonamide antibiotic, an aminoglycoside antibiotic, a macrolide antibiotic, a fluoroquinolone, and a quinolone antibiotic. Examples of a beta-lactam antibiotic include a cephalosporin, a penicillin, a monobactam, a carbapenem, and a carbacephem. Examples of aminoglycoside antibiotic include streptomycin, dihydrostreptomycin, amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisomycin, spectinomycin, tobramycin, and verdamicin. Examples of a fluoroquinolone include ciprofloxacin, clinafloxacin, enoxacin, fleroxacin, gatifloxacin, moxifloxacin, gemifloxacin, grepafloxacin, levofloxacin, norfloxacin, sparfloxacin, and trovafloxacin. Examples of a quinolone include cinoxacin, garenoxacin, and nalidixic acid. Examples of a macrolide include azithromycin, clarithromycin, dirithromycin, erythromycin, lincomycin, roxithromycin, troleandomycin, telithromycin, and spectinomycin. Examples of a tetracycline include demeclocycline, doxycycline, minocycline, oxytetracycline, tgecycline, and tetracycline. Examples of a sulfonamide antibiotic include Sulfamethizole, Sulfamethoxazole, Sulfisoxazole, and Trimethoprim-Sulfamethoxazole.

Examples of an antifungal agent include Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, efinaconazole, epoxiconazole, fluconazole, isavuconazole, itraconazole, posaconazole, propiconazole, ravuconazole, terconazole, voriconazole, abafungin, allylamines, Anidulafungin, Caspofungin, Micafungin, Aurones, Benzoic acid, Ciclopirox, Flucytosine, Griseofulvin, Haloprogin, Tolnaftate, Undecylenic acid, Crystal violet, and Balsam of Peru.

Examples of an antiviral agent useful in treating viral infections such as influenza include neuraminidase inhibitors (e.g., oseltamivir and zanamivir) and M2 ion channel inhibitors (e.g., amantadine and rimantadine) and agents that inhibit viral replication, transcription, reverse transcription, or viral particle production. In one embodiment, the antiviral agent is selected from the group consisting (+)-Calanolide A; (+)-Dihydrocalanolide A; 145U87; 2'-C-methyl-7-deazaadenosine; 2'-C-Methylcytidine; 2-Nor-cyclic GMP; 3,4-Dicaffeoylquinic acid; 3-Hydroxymethyl dicamphanoyl khellactone; 3-Hydroxyphthaloyl-beta-lactoglobulin; 3-Nitrosobenzamide; 4-Azidothymidine; 4-Methyl dicamphanoyl khellactone; 524C79; 739W94; A 160621; A 315675; A 315677; A 5021, A 74259; A 7704; A 77003; A 80735; A 80987; A 91883A; A 98881; A-837093; Abacavir; AC 2; Acemannanl Acetylcysteine-Zambon; ACH 126445; ACH 126447; Aciclovir (e.g., extended release, controlled release, topical patch); Aciclovir-PMPA; ACP HIP; Actinohivin; AD 439; AD 519; Adamantylamide dipeptide; Adefovir (e.g., dipivoxil); ADS J1; Afovirsen; AG 1284; AG 1350; AG 1478; AG 1859; AG 555; AG 6840; AG 6863; AG-021541; AGT-1; AHA 008; Aidfarel; AL 721; Alamifovir; Albuferon; Albumin/interferon-alpha; Aldesleukin; ALN RSV01; Alovudine; Alpha HGA; Alpha-IPDX; Alpha-antitrypsin; Alvircept sudotox; Alvocidib; ALX 0019; ALX 404C; AM 285; AM 365; Amantadine; AMD 070; AMD 3329; AMD 3465; AMD 8664; Amdoxovir; Amidinomycin; Aminopeptidase; Amitivir; Ampligen; Amprenavir; AMZ 0026; ANA 971; ANA 975; Ancriviroc; Andrographis; Anti-CCRS monoclonal antibody; Anti-CCRS/CXCR4 sheep monoclonal antibody; Anti-CD3 monoclonal antibody CD4IgG conjugate; Anti-CD4 monoclonal antibody; Anti-CD7 monoclonal antibody; Anti-CD8 monoclonal antibody; Anti-CMV monoclonal antibody; Anti-hepatitis B ribozyme; Anti-HIV catalytic antibody; Anti-HIV immunotoxin (IVAX); Anti-HIV-1 human monoclonal; antibody 2FS; Anti-HIV-1 human monoclonal; antibody 2G12; Anti-HIV-1 human monoclonal; antibody 4E10; Antineoplaston AS2 1 (e.g., oral); Anti-RSV antibody (Intracel, Corp.); Antisense oligonucleotide PB2; AUG; Aop-RANTES; Aphidicolin; Aplaviroc; Apricitabine; AQ 148; AR 132; AR 177; ARB 95214; ARB 97265; ARB 97268; Arbidol; ARQ 323; Artemether; Atermisinin; Artesunate; AS 101; AT 61; Atazanavir; Atevirdine; Atorvastatin; AV 1101; AV 2921; AV 2923; AV 2925; AV 2927; Avarol; AVI 4065; AVR 118; AXD 455; Azidodideoxyguanosine; Azodicarbonamide; Bafilomycin A1; Baicalin; Bavituximab; BAY 414109; BAY 439695; BAY 504798; BAY Z 4305; BB 10010; BB 2116; BCH 10652; BCH 371; BCH 527; BCTP; BCX 140; BCX 1591; BCX 1827; BCX 1898; BCX 1923; BEA; BEA 005; Bellenamine; Benanomicin A; Benzalkonium (e.g., chloride); Benzalkonium chloride/octoxynol 9 (e.g., vaginal gel); Beta-D-FDOC; Beta-L-ddC; Beta-L-FddC; Bevirimat; BG 777; BGP 15; BILA 2185 BS; BILN 303 SE; BILR 355; BIRM ECA 10-142; BIVN 401; BL 1743; BLX 833 (e.g., controlled release); BM 510836; BMS 181167-02; BMS 181184; BMS 182193; BMS 186318; BMS 187071; BMS 488043; BMS 806; BMY 27709; Boceprevir (SCH 503034);

Brecanavir; Brefeldin A; Brequinar; Brivudine; BRL 47923DP; BSL 4; BST 500L; BTA 188; BTA 798; C 1605; C 2507; C31G; Calcium spirulan; Canventol; Capravirine; Carbendazim; Carbocyclic deazaadenosine; Carbopol polymer gel; Carbovir; CC 3052; CD4 fusion toxin; CD4 IgG; CD4-ricin chain A; Celgosivir; CellCept; Cellulose sulfate; Cepharanthine; Ceplene; CF 1743; CFY 196; CGA 137053; CGP 35269; CGP 49689; CGP 53437; CGP 53820; CGP 57813; CGP 61783; CGP 64222; CGP 70726; CGP 75136; CGP 75176; CGP 75355; Chloroquine (e.g., phosphate); CI 1012; CI 1013; Cidofovir; Ciluprevir (BILN 2061); Civacir; Civamide; CL 190038; CL 387626; Clevudine; CMV 423; CMX 001; CNBA-Na; CNJ 102; Cobra venom peptide; Colloidal silver; Conocurvone; Cosalane; Costatolide; CP 1018161; CP 38; CP 51; CPFDD; CpG 10101; CRL 1072; Crofelemer; CS 8958; CS 92; CT 2576; CTC 96; Curcumin; Curdlan sulfate; Cyanovirin-N; Cyclosporine; CYT 99007; Cytarabine; Cytomegalovirus immune globulin; DAB486interleukin-2; DABO 1220; Dacopafant; DAP 30; DAP 32; Dapivirine; Darunavir; D-aspartic-beta-hydroxamate; DB 340; DDCDP-DG; DDGA; Deazaadenosine; Deazzaneplanocin A; DEB 025; DEBIO-025; Delavirdine; Delmitide; Denileukin diftitox; Deoxyfluoroguanosine; DES 6; Dexelvucitabine; Dextran sulfate; Dextrin 2-sulfate; DG 35; Didanosine; Dideoxyadenosine; Dideoxyguanosine; Dideoxythymidine; Didox; Dihydroartemisinin; Dihydrocostatolide; Dinitrochlorobenzene; DL 110; DMP 323; DMP 850; DMP 851; DmTr-ODN12; Docosanol; DP 107; DPC 082; DPC 083; DPC 681; DPC 684; DPC 961; DPC 963; Droxinavir; DUP 925; DYE; E 913; EB-Foscarnet; Edodekin alfa; Edoxudine; E-EPSEU; Efavirenz; EGS 21; EHC 18; EHT 899; Elvucitabine; EM 1421; EM 2487; Emivirine; Emtricitabine; Emtricitabine/tenofovir disoproxil fumarate; EMZ 702; Enfuvirtide; Entecavir; Eosinophil-derived neturalizing agent; Episiastatin B; ET 007; Etanercept; Ether lipid analogue; Etoviram; Etravirine; F 105; F 36; F 50003; Famciclovir; Fas-ligand inhibitor; Fasudil; Fattiviracin A1; FEAU; Feglymycin; Felvizumab; FGI 345; Fiacitabine; Fialuridine; FLG; Floxuridine; Flutimide; Fluvastatin (e.g., sodium); Fornivirsen; Fosalvudine tidoxil; Fosamprenavir; Foscarnet Sodium; Fozivudine; FP 21399; F-PBT; FPMPA; FPMPDAP; FR 191512; FR 198248; Galactan sulfate; Ganciclovir; GAP 31; GCA 186; GCPK; GE 20372A; GE 20372B; GEM 122; GEM 132; GEM 144; GEM 92; GEM 93; Gemcitabine (e.g., hydrochloride); Ginseng; Glamolec; Glutathionarsenoxide; Glycovir; Glycyrrhizin; GMDP; GO 6976; GO 7716; GO 7775; Gossypol; GPG-NH2; GPI 1485; GPI 2A; GPs 0193; GR 137615; GR 137615; GR 92938X; GS 2838; GS 2992; GS 3333; GS 3435; GS 4071; GS 438; GS 7340; GS 9005; GS 9132; GS 9160; GS 930; GW 275175; GW 5950X; HB 19; HBT 946; HCV 086; HCV 371; HCV AB 68; HCV-796; HCV-SM; HE 2000; HE 317; Hepatitis B immune globulin; Hepatitis C immune globulin; Hepex C; HEPT; Heptazyme; HGS-H/A27; HI 236; HI 240; HI 244; HI 280; HI 346; HI 443; HI 445; Histamine; Histamine dihydrochloride (e.g., injection, oral); HIV DNA vaccine (Antigen Express, Inc.); HIV immune globulin; HIV immune plasma; HL 9; HOE BAY 793; HRG 214; HS 058; HuMax-HepC; Hydroxycarbamide; Hydroxychloroquine; Hypericin; I 152; IAZT; ICN 17261; IDN 6556; Idoxuridine; IM28; Imiquimod; ImmStat; ImmuDyn; Immunocal; Imreg 1; Incadronic acid; INCB 9471; Indinavir; Infliximab; Influenza matrix protein Zn2+ finger peptide; Ingenol Triacetate; Inophyllum B; Inosine pranohex; Interferon; Interferon Alfa-2a; Interferon alfa-2b (e.g., inhalation); Interferon alfacon-1; Interferon alpha (e.g., sustained release, intranasal, Omniferon); Interferon alpha-2b (e.g., controlled release or tranadermal); Interferon alpha-2b gene therapy; Interferon alpha-n3; Interferon beta-1a; Interferon beta-1b; Interferon gamma-1b; Interferon omega; Interferon-tau; Interleukin 10 (e.g., human recombinant); Interleukin-1 receptor type I; Interleukin-13; Interleukin-15; Interleukin-16; Interleukin-2 agonist; Interleukin-4; IPdR: Ipilimumab; Isatoribine; ISIS 13312; ISIS 14803; Iso ddA; ITI 002; ITI 011; ITMN-191; JBP 485; JCA 304; JE 2147; JM 1596; JM 2763; JTK 003; JTK 109; JTK 303; K 12; K 37; K 42; Kamizol kethoxal; Kijimicin; Kistamicin; KKKI 538; KM 043; KNI 102; KNI 241; KNI 272; KNI 413; KNI 684; Kootikuppala; KP 1461; KPC 2; KPE 00001113; KPE 02003002; KRH 1120; L 689502; L 693549; L 696229; L 696474; L 696661; L 697639; L 697661; L 708906; L 731988; L 732801; L 734005; L 735882; L 738372; L 738684; L 738872; L 739594; L 748496; L 754394; L 756423; L 870810; L HAS ara AMP; Lactoferrin; Lamivudine; Lamivudine/abacavir; Lamivudine/zidovudine; Lamivudine/zidovudine/abacavir; Lasinavir; LB 71116; LB 71148; LB 71262; LB 71350; LB 80380; LB 84451; L-chicoric acid; Lecithinized superoxide dismutase; Leflunomide; Lentinan; Leukocyte interleukin injection (CEL-SCI Corp.); Leukotriene B4-LTB4; Levcycloserine; Levofloxacin; Lexithromycin; Licorice root; Liposomal ODG-PFA-OMe; Lithium succinate; Lobucavir; Lodenosine; Lopinavir; Lovastatin; Loviride; Lufironil; LY 180299; LY 214624; LY 253963; LY 289612; LY 296242; LY 296416; LY 309391; LY 309840; LY 3111912; LY 314163; LY 314177; LY 316683; LY 326188; LY 326594; LY 326620; LY 338387; LY 343804; LY 354400; LY 355455; LY 366094; LY 366405; LY 368177; LY 73497; Lysozyme; M 40401; M4N; Madu; Mannan sulfate; MAP 30; Maraviroc; Maribavir; Masoprocol; MB-Focarnet; MC 207044; MC 207044; MC 207685; MC 867 mCDS71; MDI-P; MDL 101028; MDL 20610; MDL 27393; MDL 73660; MDL 74428; MDL 74695; MDL 74968; MDX 240; ME 3738; ME 609; MEDI 488; Medusa Interferon; MEN 10690; MEN 10979; MER N5075A; Merimepodib (VX-497); Met-enkephalin; Methisazone; Mevastatin; MGN 3; Michellamine B; Miglustat; Milk thistle; Mitoquinone; MIV 150; MIV 210; Mivotilate; MK 0518; MK 944A; MM 1; MMS 1; MOL 0275; Monoclonal antibody 1F7; Monoclonal antibody 2F5; Monoclonal antibody 3F12; Monoclonal antibody 447-52D; Monoclonal antibody 50-61A; Monoclonal antibody B4; Monoclonal antibody HNK20; Monoclonal antibody NM01; Mopyridone; Moroxydine; Motavizumab; Motexafin gadolinium; Mozenavir; MPC 531; MRK 1; MS 1060; MS 1126; MS 8209; MS 888; MSC 127; MSH 143; MTCH 2; MTP-PE; Murabutide; MV 026048; MX 313; Mycophenolate mofetil; Mycophenotic Acid; Navuridine; NB 001; Nalfinavir (e.g., mesylate); Neomycin B-arginine conjugate; Neotripterifordin; Nevirapine; NIM 811; Nitazoxanide; Nitric oxide (e.g., ProStrakan); Nitrodeazauridine; NM 01; NM 49; NM 55; N-nonyl-DNJ; NNY-RANTES; Nonakine; NOV 205; NP 06; NP 77A; NPC 15437; NSC 158393; NSC 158393; NSC 20625; NS 287474; NSC 4493; NSC 615985; NSC 620055; NSC 624151; NSC 624321; NSC 627708; NSC 651016; NSC 667952; NSC 708199; NV 01; NV-08; Octoxynol 9; OCX 0191; OH 1; OKU 40; OKU 41; Oltipraz; OMaciclovir; Opaviraline; OPT TL3; Oragen; ORI 9020; Oseltamivir; Oxetanocin; Oxothiazolidine carboxylate; P 56; PA 344/PA 344B; Palinavir; Palivizumab; PAMBAEEG; Papuamide A; PBS 119; PC 1250; PC 515; PCL 016; PD 0084430; PD 144795; PD 153103; PD 157945; PD 169277; PD 171277; PD 171791; PD 173606; PD 173638; PD 177298; PD 178390; PD 178392; PD 190497; Pegaldesleukin; Peginterferon alfa-2a; Peginterferon alfa-2b; PEGinterferon alfacon-1; PEGylated interferon; Pegylated thymalfasin; Peldesine; PEN 203; Penciclovir; Pentosan polysulfate; Pentoxifylline; Peptide T; Peramivir; PETT 4; PF-03491390; PG 301029; PG 36; Phellodendrine; Phosphatidyllamivudine; Phosphatidylzalcitabine; Phosphatidylzidovudine; Phosphazid; Phosphinic cyclocreatine; Pinosylvin; Pirodavir; PL 2500; Pleconaril; Plerixafor; PM 104; PM 19; PM 523; PM 92131; PM 94006; PEDAP; PMS 601; PMTG; PMTI; PN 355; PNU 103657; PNU 142721; podophylltoxin; Poly ICLC; Polyadenylic polyuridylic acid; Polysaccharide K; PP 29; PPB 2; PPL 100; Pradefovir; Pradimicin A; Prasterone; PRO 140; PRO 2000; PRO 367; PRO 542; Probucol (Vyrex Corp.); Propagermanium; Prostratin; Pseudohypericin; PSI 5004; PSI-6130; PTPR; PTX 111; Pyriferone; Q 8045; QM 96521; QM 96639; AR 435; Quinbene; Quinxapeptin A; Quinoxapeptin B; QYL-438; QYL-609; QYL-685; QYL-769; R 1518; R 1626; R 170591; R 18893; R 61837; R 71762; R 803; R 82150; R 82913; R 851; R 87366; R 91767; R 944; R 95288; R-1626; R7128; Raluridine; Ramatroban; Ranpirnase; RB 2121; RBC CD4; RD 30028; RD 42024; RD 42138; RD 42217; RD 42227; RD 62198; RD 65071; RD6 Y664; Regavirumab; Resiquimod; Resobene; Respiratory syncytial virus immune globulin; Retrogen; REV 123; RFI 641; Ribavirin; Rilpivirine; Rimantadine; Ritonavir; RKS 1443; RO 0334649; RO 247429; RO 250236; RO 316840; RO 54445; Robustaflavone; Rolipram; Rosiglitazone; RP 70034; RP 71955; RPI 312; RPI 856; RPR 103611; RPR 106868; RPR 111423; RS 654; RS 980; RSV 604; Rubitecan; Rupintrivir; S 1360; S 2720; S 9a; SA 1042; SA 8443; Saquinavir (e.g., mesylate); Sargramostim; S 180922; SB 205700; SB 206343; SB 73; SC 49483; SC 55099; SCH 350634; SCH 6; Schisandra; SCV 07; SCY-635; SD 894; S-DABO; SDF 1; SDZ 282870; SDZ 283053; SDZ 283471; SDZ 89104; SDZ PRI 053; SE 063; Semapimod; Sevirumab; SF 950; SF 953; Siamycin 1; Siamycin 2; sICAM-1; Sifuvirtide; SIGA 246; Silipide, Simvastatin; Simvastatin hydroxyl acid, ammonium salt; Sizofiran; SJ 3366; SK 034; SKF 108922; SKI 1695; SO 324; Sodium laurilsulfate; Solutein; Sorivudine (e.g., tropical); SP 10; SP 1093V; Sparfosic acid; SPC 3; SPD 756; SpecifEx-Hep B; SPI 119; SPL 2992; SPL 7013; SPV 30; SR 10204; SR 10208; SR 11335; SR 3745A; SR 3773; SR 3775; SR 3784; SR 3785; SR 3785; SR 41476; SRL 172; SRR SB3; ST 135647; Stachyflin stallimycin; Stampidine; Statolon; Stavudine; Steponin; Suksdorfin; Sulfated maltoheptaose; Superoxide dismutase; Suramin (e.g., sodium); Sy 801; T 1100; T 118; T 22; T 30695; T 611; T 705; T4GEN; Tacrine; TAK 220; TAK 652; TAK 779; Talviraline; TAP 29; Taribavarin; TASP; Tecleukin; Tecogalan (e.g., sodium); TEI 2306; Telaprevir (VX-950); Telbivudine; Telinavir; Temacrazine; Tenidap; Tenofovir; Tenofovir disoproxil fumarate; TGG II 23A; TH 9407; TH 9411; Thalidomide; Thiophosphonoformic acid; Thiovir; Thymalfasin (e.g., Zadaxin); Thymoctonan; Thymosin fraction 5; Thymotrinan; Thymus extract; tICAM-1; Tifuvirtide; Tilarginine; Tipranavir; Tiviciclovir; Tivirapine; TJ 41; TJ 9; TL 3024; TMC 126; TNF-alpha inhibitor; TNK 6123; TNX 355; Todoxin; TOFA; Tomeglovir; Transforming growth factor-alpha; TraT; Trecovirsen; Tremacamra; Trichosanthin; Triciribine; Triconal; Trifluridine; Trimidox; Trodusquemine; Tromantadine; Trovirdine; Tucaresol; Tunicamycin; Tuvirumab; U 103017; U 75875; U 78036; U 80493; U 81749; U 88204E; U 96988; U 9843; UA 926; Ubenimex; UC 10; UC 16; UC 38; UC 42; UC 68; UC 70; UC 781; UC 81; UC 82; UIC 94003; Ukrain; UL36ANTI; UMJD 828; Ursodeoxycholic acid; UT 231B; Valaciclovir; Valganciclovir; Valopicitabine (NM 238); Valopicitabine (NM-238); Valtorcitabine; Varicella zoster immune globulin; VB 19038; Vesnarinone; VF 1634; VGV 1; VGX 410; Vicriviroc; Vidarabine; Vincristine (e.g., sulfate); VIR 101; Viraprexin; Virodene; Virostat; Viscum album extract; VP 50406; VRT 21493; VRX 496; VX 10166; VX 10217; VX 10493; VX 11106; WF 10; WHI 05; WHI 07; WIN 49569; WIN 49611; WM 5; WR 151327; XK 216; XK 234; XN 482; XP 951; XQ 9302; XR 835; XTL 2125; XTL 6865; XU 348; XU 430; Y-ART-3; YHI 1; YK FH312; Z 100; Z 15; Zalcitabine; Zanamivir; Zidovudine (e.g., phosphate-didanosine dimer); Zidovudine triphosphate mimics; ZX 0610; ZX 0620; ZX 0791; ZX 0792; ZX 0793; ZX 0851; ZY II, and combinations thereof.

In one embodiment, the antiviral agent is selected from the group consisting Abacavir, Acyclovir (Aciclovir), Adefovir, Amantadine, Amprenavir (Agenerase), Ampligen, Arbidol, Atazanavir, Atripla, Balavir, idofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Novir, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine and combinations thereof.

Examples of anti-parasitic agents include Bephenium, Diethylcarbamazine, Ivermectin, Niclosamide, Piperazine, Praziquantel, Pyrantel, Pyrvinium, Albendazole, Flubendazole, Mebendazole, Thiabendazole, Benzyl benzoate, Benzyle benzoate/disulfiram, Lindane, Malathion, Permethrin, Benzyl alcohol, Piperonyl butoxide/pyrethrins, Spinosad, and Crotamiton.

The dipivefrin used in any of the methods disclosed herein can be the freebase or a pharmaceutically acceptable salt thereof. Preferably the dipivefrin salt is an acid addition salt, for example, dipivefrin hydrochloride. The dipivefrin can be racemic dipivefrin or optically purified D- or L-dipivefrin, preferably L-dipivefrin.

Furthermore, the dipivefrin can be isotopically labeled with a pharmaceutically acceptable isotopic label. Examples of isotopes suitable for inclusion in the isotopically labeled dipivefrin, or salt or derivative thereof, include isotopes of hydrogen, such as $^{2}$H and $^{3}$H; carbon, such as $^{11}$C, $^{13}$C and $^{14}$C; chlorine, such as $^{36}$Cl; nitrogen, such as $^{13}$N and $^{15}$N; and oxygen, such as $^{15}$O, $^{17}$O and $^{18}$O. Isotopically-labeled dipivefrin can be prepared by conventional techniques known to those skilled in the art.

Certain isotopically-labeled dipivefrin, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection. Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$ $^{15}O$ and $^{13}N$, can be useful in Positron Emission Topography (PET) studies for examining substrate receptor occupancy.

Also disclosed is a composition comprising the dipivefrin or a pharmaceutically acceptable salt, solvate, clathrate, polymorph, analog, prodrug or derivative thereof. The composition may be suitable for pharmaceutical use and may be in the form of a pharmaceutical composition. The pharmaceutical composition may have any suitable form, and may be a tablet, capsule, lyophilized solid, solution, suspension, or a combination thereof. The pharmaceutical composition may be an intravenous, injectable, topical, or oral dosage form. The pharmaceutical composition may be a dosage form intended for parenteral administration, such a lyophilized solid needing reconstitution before administration or a reconstituted solution of the lyophilized solid. The pharmaceutical composition may be an oral dosage form in the form of a tablet or capsule. In a preferred embodiment, the dipivefrin is formulated into any oral dosage form including solid, semi-solid, liquid, powder, sachet and the like. Solid oral dosage forms can include, for example, a tablet, a capsule (hard or soft), or subunits, and the like. "Subunit" includes a minitablet, a bead, a spheroid, a microsphere, a seed, a pellet, a caplet, a microcapsule, a granule, a particle, and the like that can provide an oral dosage form alone or when combined with other subunits. Exemplary semi-solid or liquid dosage forms include a suspension, a solution, an emulsion, and the like. Solid oral dosage forms can also include orally dissolving/disintegrating dosage (ODT) forms. Exemplary ODTs include orally dissolving/disintegrating tablets, orally dissolving films and dosage forms intended for sublingual/lingual/buccal delivery such as fast dissolving/disintegrating sublingual tablets and films.

The oral dosage form can be formulated for a specific type of release including immediate-release, controlled-release, sustained-release, or extended-release.

The pharmaceutical composition comprising a dipivefrin composition may be used in any of the method disclosed herein.

The dipivefrin composition is generally present within a pharmaceutical composition in a therapeutically effective amount. As used herein, a "therapeutically effective amount" is an amount that, upon administration to a patient, results in a discernible patient benefit. An effective amount of a dipivefrin composition can range from about 0.001 mg/kg to about 1000 mg/kg, about 0.01 mg/kg to about 100 mg/kg, about 10 mg/kg to about 250 mg/kg, about 0.1 mg/kg to about 15 mg/kg; or any range in which the low end of the range is any amount between 0.001 mg/g and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

The pharmaceutical compositions can be prepared by a process comprising combining the dipivefrin with a pharmaceutically acceptable excipient. Thus, the disclosure further encompasses the use of the above-described dipivefrin composition in the manufacture of a pharmaceutical composition. Excipients may be added to facilitate manufacture, enhance stability, enhance product characteristics, enhance bioavailability, enhance patient acceptability, etc. Pharmaceutical excipients include carriers, fillers, binders, disintegrants, lubricants, glidants, granulating agent, compression aids, colors, sweeteners, preservatives, suspending agents, dispersing agents, film formers, flavors, printing inks, buffer agents, pH adjusters, taste masking agents etc. In some instances, a single material will meet two or more of the foregoing general classifications.

Also disclosed is a combination pharmaceutical composition comprising a dipivefrin and at least one other active agent and at least one pharmaceutical excipient.

In practicing the methods of treatment or use provided herein, therapeutically effective amounts of the compounds disclosed herein are administered to a mammal having a disease, disorder, or condition to be treated. In some embodiments, the mammal is human. The therapeutically effective amounts of the compounds may vary depending on the compounds, the severity of the disease, the age and relative health of the subject, and other factors.

The term "combination" as used herein, means a product that results from the mixing or combining of dipivefrin and any additional therapeutic agents and includes both fixed and non-fixed combinations. The term "fixed combination" means that dipivefrin and the additional therapeutic agents are administered in a single entity or dosage form. The term "non-fixed combination" means that dipivefrin and the additional therapeutic agents are administered as separate entities or dosage forms either simultaneously, concurrently or sequentially with no specific intervening time limits, wherein such administration provides therapeutically effective levels of the two compounds in the body of the patient. The latter also applies to cocktail therapy, e.g. the administration of three or more active ingredients.

In some embodiments, the pharmaceutical combination and/or composition described herein also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some embodiments, the pharmaceutical combination and/or compositions also include one of more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical formulations described herein can be administered to a subject by multiple administration routes, including but not limited to, oral, parenteral (e.g., intravenous, subcutaneous, intramuscular), intra, buccal, sublingual, topical, rectal, inhalation or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, pharmaceutical combination and/or compositions including a compound described herein are manufactured in a conventional manner, such as, by way of example only, by means of conventional mixing, dissolving, granulating, dragee-making, levigating, emulsifying, encapsulating, entrapping or compression processes.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In some embodiments, compositions provided herein also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide, cetylpyridinium chloride and the parabens.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosane polysulfate and other heparinoids, (m) cyclodextrins, (1) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydrocypropylmethylcellulose, hydroxyethylcellulose, hydroxypropylcellulose (e.g., Klucel®), ethylcellulose (e.g., Ethocel®) and microcrystalline cellulose (e.g., Avicel®); microcrystalline dextrose; amylose; magnesium aluminum silicate: polysaccharide acids; bentonites; gelatin; polycinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isabgol husks, polyvinylpyrrolidone (e.g., Polycidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of dipivefrin, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" include, but are not limited to, acacia, gelatin, colloidal silicon dioxide, calcium glycerophosphate, calcium lactate, maltodextrin, glycerin, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pegelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include material that control the diffusion and homogeneity of a drug through liquid media or a granulation method or blend method. IN some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HP MCAS), non-crystalline cellulose, magnesium aluminum silicate, triethanolamine, polyvinyl alcohol (PVA), vinyl pyrrolidone/vinyl acetate copolymer (s630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as e.g., gum tragacanth and gum acacia, guar gum, xanthans, including xanthan gum, sugars, cellulosics, such as, e.g., sodium carboxymethylcellulose, polysorbate-80, sodium alginate, polyethoxylated sorbitan monolaurate, polyethoxylated sorbitan monolaurate, povidone, carbomers, polyvinyl alcohol (PVA), lginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel; dibasic calcium phosphate, dicalcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar'; monobasic calcium sulfate monohydrate, calcium sulfate dehydrate; calcium sulfate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system and a drug diffusing into the bloodstream through tissues under the tongue or through the oral mucosa.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple marshmallow, menthol. Mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti frutti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, µg, ng, or pg/ml "Pharmacodynamics" refers to the factors which determine the biologic response observed relative to the concentration of drug at a site of action of therapeutic agent per mL, dL, or L of blood serum, absorbed into the bloodstream after administration. As used herein, measurable plasma concentrations are typically measured in pg/ml, ng/ml or µg/ml.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as tracetin, triethylcitrate, ethyl oleate, ethyl caprylate, sodium lauryl sulfate, sodium docusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, Captisol, ethanol, n-butanol, isopropyl alcohol, cholesterol, bile slats, polyethylene glycol 200-600, glycofurol, transcutol, propylene glycol, and dimethyl isosorbide and the like.

"Stabilizers" include compounds such as any anti-oxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethycellulose, methylcellulose, hydroypropylmethylcellulose, hydroxymethylcellulose acetate stearate, polysorbate-80, hydroxymethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile slats, glyceryl monostearate, copolymers of ethylene oxide and propylene oxide, e.g., Pluronic® (BASF), and the like. Some other surfactants include polyoxyethylene fatty acid glycerides and vegetable oils, e.g. polyoxyethylene (60) hydrogenated castor oil; and polyoxyethylene alkylethers and alkyphenyl ethers, e.g., octoxynol 10, octoxynol 40. In some embodiments, surfactants are included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan, monolaurate, triethanolamine oleate, polyxyethylene sorbitan monooleate, polyoxyethylene sorbitan monolaurate, sodium docusate, sodium oleate, sodium lauryl sulfate, sodium docusate, triacetin, Tween 80, vitamin E TPGS, ammonium salts and the like.

Formulations

The formulations of dipivefrin compositions include those suitable for oral, parenteral (including subcutaneous, intradermal, intramuscular, intravenous, intraarticular, and intramedullary), intra peritoneal, transmucosal, transdermal, rectal, pulmonary, nasal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject disclosure or a pharmaceutically acceptable salt, or solvate, hydrate, prodrugs, analogs and derivatives thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of dipivefrin compositions suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion or submicron particles suspended in aqueous or non-aqueous liquid or complexes with cyclodextrins. The active ingredient may also be presented as a bolus, electuary or paste.

Pharmaceutical preparations of dipivefrin compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

Pharmaceutical preparations of dipivefrin compositions may be formulated for oral administration as orally dissolving tablets or orally disintegrating tablets (ODTs). ODTs differ from traditional tablets in that they are designed to be dissolved on the tongue or disintegrate in the mouth rather than swallowed whole. The ODT serves as an alternative dosage form for patients who experience dysphagia (difficulty in swallowing) or for where compliance is a known issue and therefore an easier dosage form to take ensures that medication is taken. ODTs also have a faster onset of action due to pre-gastric absorption and potentially improved pharmacokinetics than tablets or capsules and have the convenience of a tablet that can be taken without water.

Manufacturing processes for orally dissolving dosage forms containing dipivefrin compositions suitable for oral, buccal, lingual and sublingual administration are known in the art and include, but are not limited to, conventional tableting techniques, freeze-dried technology, and floss-based tableting technology.

Conventional tablet processing features conventional tablet characteristics for ease of handling, packaging, and fast disintegration (T. K. Ghosh, Oct. 29, 2003, American Association of Pharmaceutical Scientists). The technology is based on a combination of physically modified polysaccharides that have water dissolution characteristics that facilitate fast disintegration and high compressibility. The result is a fast-disintegrating tablet that has adequate hardness for packaging in bottles and easy handling. In certain embodiments, the manufacturing process involves granulating low-moldable sugars (e.g., mannitol, lactose, glucose, sucrose, and erythritol) that show quick dissolution characteristics with high-moldable sugars (e.g., maltose, sorbitol, trehalose, and maltitol). The result is a mixture of excipients that have fast-dissolving and highly moldable characteristics (Hamilton et al., 2005, Drug Deliv. Technol. 5: 34-37). The dipivefrin can be added, along with other standard tableting excipients, during the granulation or blended processes. The tablets are manufactured at a low compression force followed by an optional humidity conditioning treatment to increase tablet hardness (Parakh, et al., 2003, Pharm. Tech. 27: 92-100).

In other embodiments, a compressed oral, buccal or sublingual tablet comprising dipivefrin is based on a conventional tableting process involving the direct compression of active ingredients, effervescent excipients, and taste-masking agents. The tablet quickly disintegrates because effervescent carbon dioxide is produced upon contact with moisture. The effervescent excipient (known as effervescence couple) is prepared by coating the organic acid crystals using a stoichiometrically lesser amount of base material. The particle size of the organic acid crystals is carefully chosen to be larger than the base excipient to ensure uniform coating of the base excipient onto the acid crystals. The coating process is initiated by the addition of a reaction initiator, which is purified water in this case. The reaction is allowed to proceed only to the extent of completing the base coating on organic acid crystals. The required end-point for reaction termination is determined by measuring carbon dioxide evolution. Then, the excipient is mixed with the active ingredient or active microparticles and with other standard tableting excipients and then compressed into tablets.

In still other embodiments, the oral, buccal or sublingual tablets are made by combining non-compressible fillers with a taste-masking excipient and active ingredient into a dry blend. The blend is compressed into tablets using a conventional rotary tablet press. Tablets made with this process have higher mechanical strength and are sufficiently robust to be packaged in blister packs or bottles (Aurora et al., 2005. Drug Deliv. Technol. 5:50-54). In other embodiments, the method further incorporates taste-masking sweeteners and flavoring agents such as mint, cherry, and orange. In certain embodiments, dipivefrin tablets made with this process should disintegrate in the mouth in 5-45 seconds and can be formulated to be bioequivalent to intramuscular or subcutaneous dosage forms containing epinephrine.

The freeze-drying process involves the removal of water (by sublimation upon freeze drying) from the liquid mixture of a drug (e.g., dipivefrin), matrix former, and other excipients filled into preformed blister pockets. The formed matrix structure is very porous in nature and rapidly dissolves or disintegrates upon contact with saliva (Sastry, et al., 2005, Drug Delivery to the Oral Cavity: Molecule to Market, pp. 311-316). Common matrix-forming agents include gelatins, dextrans, or alginates which form glassy amorphous mixtures for providing structural strength; saccharides such as mannitol or sorbitol for imparting crystallinity and hardness; and water, which functions as a manufacturing process medium during the freeze-drying step to induce the porous structure upon sublimation. In addition, the matrix may contain taste-masking agents such as sweeteners, flavorants, pH-adjusting agents such as citric acid, and preservatives to ensure the aqueous stability of the suspended drug in media before sublimation. In this embodiment, Freeze-dried orally dissolving/disintegrating dosages comprising dipivefrin can be manufactured and packaged in polyvinyl chloride or polyvinylidene chloride plastic packs, or they may be packed into laminates or aluminum multilaminate foil pouches to protect the product from external moisture.

Other known methods for manufacturing ODTs include lyophilization (e.g., Lyoc (Farmalyoc, now Cephalon, Franzer, Pa.) and QuickSolv (Janssen Pharmaceutica, Beerse, Belgium). Lyoc is a porous, solid wafer manufactured by lyophilizing an oil-in-water emulsion placed directly in a blister and subsequently sealed. The wafer can accommodate high drug dosing and disintegrates rapidly but has poor mechanical strength (see EP 0159237). QuickSolv tablets are made with a similar technology that creates a porous solid matrix by freezing an aqueous dispersion or solution of the matrix formulation. The process works by removing water using an excess of alcohol (solvent extraction).

In other embodiments, floss-based tablet technology (e.g., FlashDose, Biovail, Mississauga, ON, Canada) can be used to produce fast-dissolving lingual, buccal or sublingual tablets comprising dipivefrin using a floss known as the shearform matrix. This floss is commonly composed of saccharides such as sucrose, dextrose, lactose, and fructose. The saccharides are converted into floss by the simultaneous action of flash-melting and centrifugal force in a heat-processing machine similar to that used to make cotton candy. See U.S. Pat. Nos. 5,587,172, 5,622,717, 5,567,439, 5,871,781, 5,654,003, and 5,622,716, each of which is specifically incorporated by reference herein in their entirety. The fibers produced are usually amorphous in nature and are partially re-crystallized, which results in a free-flowing floss. The floss can be mixed with dipivefrin and pharmaceutically acceptable excipients followed by compression into a tablet that has fast-dissolving characteristics.

Additional techniques can also be used to formulate the rapidly disintegrating or dissolving lingual, buccal or sublingual tablets of the present invention (Sastry, et al., 2000, Pharm Sci. Technol Today 3: 138-145; Chang et al., 2000, Pharmaceutical Technology 24: 52-58; Sharma et al., 2003, Pharmaceutical Technology North American 10-15; Allen, 2003, International Journal of Pharmaceutical Technology 7: 449-450; Dobetti, 2000, Pharmaceutical Technology Europe 12: 32-42; Verma and Garg, 2001, Pharmaceutical Technology On-Line 25:1-14). Direct compression, one of these techniques, requires the incorporation of a super disintegrant into the formulation, or the use of highly water soluble excipients to achieve fast tablet disintegration or dissolution. Direct compression does not require the use of moisture or heat during tablet formation process, so it is very useful for the formulation and compression of tablets containing moisture-labile and heat-labile medications. However, the direct compression method is very sensitive to changes in the types and proportions of excipients, and in the compression force (CF), when used to achieve tablets of suitable hardness without compromising the rapid disintegration capabilities.

As will be appreciated by one of the skill in the art, in order for tablets administered sublingually to release the dose of medication for maximum rate and extent of absorption, the tablet must disintegrate almost instantaneously following insertion into the sublingual cavity. Precise selection and evaluation of the type and proportion of excipients used to formulate the tablet control the extent of harness and rate of disintegration. Compression force (CF) can also be adjusted to result in tablets that have lower hardness (H) and disintegrate more quickly. Unique packaging methods such as strip packaging may be required to compensate for the problem of extreme friability of rapidly disintegrating, direct compression tablets.

Pharmaceutical preparations of dipivefrin compositions may also be formulated as fast dissolving films (FDFs) or rapidly dissolving films or orally dissolving films (ODFs) or thin oral films for buccal, lingual and sublingual administration. These techniques are known in the art and described in, for example, U.S. Pat. Nos. 7,067,116; 7,025,983; 6,923,981; 6,596,298; and U.S. Published Application No. 20040247648, each of which is specifically incorporated herein in their entirety. In such embodiments, in addition to dipivefrin, the rapidly dissolving oral films can comprise a film-forming agent, and at least one of the following additional ingredients: water, antimicrobial agents, plasticizing agents, flavoring agents, saliva stimulating agents, cooling agents, surfactants, stabilizing agents, emulsifying agents, thickening agents, binding agents, coloring agents, sweeteners, fragrances, triglycerides, preservatives, polyethylene oxides, propylene glycol, and the like. By way of a non-limiting example, the buccal, lingual, or sublingual rapidly dissolving oral films described herein can comprise a film-forming agent selected from pullulan, hydroxypropylmethyl cellulose, hydroxyethyl cellulose, hydroxypropylcellulose, polyvinyl pyrrolidone, carboxymethyl cellulose, polyvinyl alcohol, sodium alginate, polyethylene glycol, xanthan gum, tragacanth gum, guar gum, acacia gum, Arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, Zein, gluten, Soy protein isolate, whey protein isolate, casein and mixtures thereof. In certain aspects, the rapidly dissolving films can further comprise a taste-masking agent, e.g., an ion exchange resin. In certain embodiments, the ion exchange resins for use in the dissolving films of the present invention are water-insoluble and consist of a pharmacologically inert organic or inorganic matrix containing covalently bound functional groups that are ionic or capable of being ionized under the appropriate conditions of pH. The organic matrix may be synthetic (e.g., polymers or copolymers of acrylic acid, methacrylic acid, Sulfonated Styrene, Sulfonated divinylbenzene), or partially synthetic (e.g., modified cellulose and dextrans). The inorganic matrix can also be, e.g., silica gel modified by the addition of ionic groups. The covalently bound ionic groups may be strongly acidic (e.g., Sulfonic acid), weakly acidic (e.g., carboxylic acid), strongly basic (e.g., quaternary ammonium), weakly basic (e.g., primary amine), or a combination of acidic and basic groups. In still other aspects, the rapidly dissolving films can comprise modified Starches which can significantly improve the overall stability and resistance of the film to adverse factors including heat and moisture for better product performance and improved storage life. Modified starches can also enable the dissolution of more solids (up to twice the amount attainable with unmodified starch) in the buccal, lingual, or sublingual film. In certain embodiments, the modified starches include modified corn Starches, modified tapioca starches, acid and enzyme hydrolyzed corn and/or potato starches, hypochlorite-oxidized starches, acid-thinned starches, ethylated Starches, cross-bonded starches, hydroxypropylated tapioca starches, hydroxypropylated corn starches, pregelatinized modified Starches, and the like.

Pharmaceutical preparations of dipivefrin compositions suitable for buccal, lingual and sublingual administration include sublingual tablets—tablets which easily melt in the mouth, dissolve rapidly and with little or no residue; sublingual strips—similar to tablets in that they easily melt in the mouth and dissolve rapidly; multi-purpose tablets—soluble tablets for either oral or sublingual (or buccal) administration, often also suitable for preparation of injections; sublingual drops—a concentrated solution to be dropped under the tongue; sublingual spray—spray for the tongue; lozenge—effects a metered and patient-controlled-rate combination of sublingual, buccal, and oral administration; effervescent buccal or sublingual tablets—this method drives the drug through the mucous membranes much faster.

Pharmaceutical preparations may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, nanoparticle suspensions, solutions or emulsions in oily or aqueous vehicles, and may contain formulatory agents such as suspending, stabilizing, solubilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, films or gels formulated in conventional manner Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present disclosure externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose.

Pharmaceutical preparations for administration by inhalation are conveniently delivered from an insufflator, nebulizer pressurized packs or other convenient means of delivering & aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch, or large porous particles in which the active drug molecules are embedded as stabilized nanoparticles. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

The compounds or compositions described herein can be delivered in a vesicle, e.g., a liposome (see, for example, Langer, *Science* 1990, 249, 1527-1533; Treat et al., Liposomes in the Therapy of Infectious Disease and Cancer, Lopez-Berestein, Fidler and Isaiah, Ed., Liss, N.Y., pp. 353-365, 1989). The compounds and pharmaceutical compositions described herein can also be delivered in a controlled release system. In one embodiment, a pump may be used (see, Sefton, *CRC Crit. Ref. Biomed. Eng.* 1987, 14, 201; Buchwald et al. *Surgery*, 1980, 88, 507; Saudek et al. *N Engl. J. Med.* 1989, 321, 574. Additionally, a controlled release system can be placed in proximity of the therapeutic target. (See, Goodson, *Medical Applications of Controlled Release,* 1984, Vol. 2, pp. 115-138). The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. To increase aqueous solubility, a solubilizing agent such as a cyclodextrin may be included in the pharmaceutical composition. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump. The pharmaceutical compositions may be in the form of a sterile injectable aqueous or oleaginous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The sterile injectable preparation may also be a sterile injectable nanoparticle suspension in a non-toxic parenterally-acceptable diluent or solvent, for example as a nanoparticle suspension in sterile water. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the drug substance with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the disclosure can be used. As used herein, topical application can include mouth washes and gargles.

The disclosure includes an orally dissolving tablet containing dipivefrin or a dipivefrin salt such as dipivefrin HCl. The orally dissolving tablet is capable of dissolving in the oral cavity in 5 minutes or less, 2 minutes or less, 1 minute or less, or 30 seconds or less. The tablet contains (based on dipivefrin free base) 1 mg to 100 mg dipivefrin, 1 mg to 50 mg dipivefrin, 1 mg to 20 mg dipivefrin, 1 mg to 10 mg dipivefrin, 5 mg dipivefrin, or 3.0 mg dipivefrin. The orally dissolving tablet contains a water soluble polymer, such as gelatin or HPMC. The water soluble polymer can comprise 1% to 60% w/w, 1% to 50% w/w, or 10% to 50% w/w of the tablet. The tablet can contain a sweetener, such as saccharin, sucralose, aspartame, acesulfame K, maltitol, stevia, or a combination of any of the foregoing. The tablet can contain a buffer. The tablet can contain povidone, for example 1% to 30% or 5% to 25% w/w povidone. The orally dissolving tablet can be a dipivefrin or dipivefrin salt tablet capable of providing substantially the same blood level of epinephrine as a US FDA approved injectable epinephrine dosage form within 45 minutes or within 30 minutes of administration.

Pharmaceutical compositions may be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regiment. Pharmaceutical compositions may contain the active ingredient in the form of submicron/nano particles stabilized with various stabilizers such hydroxypropyl methyl cellulose (HPMC), sodium lauryl sulfate, polyvinyl alcohol. Pharmaceutical compositions may contain the active ingredient in the form of inclusion complexes with cyclodextrins.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies will be regulated according to the judgment of the attending clinician (physician) considering such factors as described above. Thus the amount of pharmaceutical composition to be administered may vary widely. Administration may occur in an amount of between about 0.001 mg/kg of body weight to about 1000 mg/kg of body weight per day (administered in single or divided doses), more preferably at least about 5 mg/kg of body weight per day. A particular therapeutic dosage of dipivefrin can include, e.g., from about 0.01 mg to about 200 mg of compound, or from about 0.05 mg to about 50 mg. The quantity of active compound in a unit dose of preparation may be varied or adjusted according to the particular application from about 0.01 mg to 150 mg, 0.01 mg to 100 mg, 0.01 mg to 50 mg, 0.1 mg to 20 mg, 0.1 mg to 10 mg, 0.1 mg to 5 mg, 0.1 mg to 3 mg, 2.5 mg, 2 mg, or 1.5 mg dipivefrin.

In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular IC50 value of the compound used. In combinational applications in which the compound is not the sole therapy, it may be possible to administer lesser amounts of compound and still have therapeutic or prophylactic effect.

This disclosure is further illustrated by the following examples, which are non-limiting.

EXAMPLES

Example 1. Pharmacokinetic Profile of Dipivefrin after Single Oral Administration in Mice Male C57BL6 mice, approximately 14 weeks of age and weighing between 28 and 31 g, were placed in an anesthesia chamber and transiently anesthetized with isoflurane (Henry Schein). After approximately 5 minutes and in the absence of reflex (toe pinch), mice were bled via retro-orbital sinus at t=0 (pre-dose). A volume of 25 μL of whole blood was taken from the retro-orbital sinus and added to 40 μL of saline supplemented with EDTA (0.125%) and sodium metabisulfite (1 mg/mL) (3.85× dilution). Mice (N=3) were then immediately dosed orally with dipivefrin chloride formulated as an aqueous solution at a dose of 21.2 mg/kg (equivalent to 10 mg/kg racemic epinephrine). Following oral administration, mice were then retro-orbital bled under anesthesia at the following time points post-dose: 15, 30, 1 h, 2 h, 4 h, and 6 h. About 45 μl of the diluted plasma was recovered and plated.

The plasma samples were analyzed for epinephrine using a validated LC/MS/MS method (Keystone Bioanalytics, North Wales Pa.). The PK analysis results of oral dipivefrin HCl are summarized in Table 1 along with those of IP and IM administration shown in Examples 2 and 3.

TABLE 1

| Summary of PK analysis results of dipivefrin HCl in mice (data presented as mean ± SEM) | | | | | |
|---|---|---|---|---|---|
| Test articles | Route of administration | Dose | $C_{max}$ (ng/ml) | $T_{max}$ (min) | $AUC_{last}$ (ng min/ml) |
| Dipivefrin HCl | Oral gavage | 21.2 mg/kg | 23.41 ± 9.35 | 40.0 ± 10 | 2174.65 ± 645.12 |
| Dipivefrin HCl | IM | 0.636 mg | 1741.05 ± 1219.80 | 8.3 ± 3.3 | 93139.18 ± 18290.22 |
| Dipivefrin HCl | IP | 1.06 mg/kg | 23.31 ± 3.88 | 15 ± 0 | 1539.96 ± 407.39 |

FIG. 1 shows mean plasma epinephrine concentration at T0 (pre-dose), 15, 30 min, 1, 2, 4, and 6 h time points. This example together with Example 2 and 3 demonstrates that dipivefrin was absorbed and biotransformed into epinephrine rapidly after oral, IM and IP administration.

Example 2. Pharmacokinetic Profile of Dipivefrin after Single I.P. Injection in Mice Male C57BL6 Mice roughly 14 weeks of age and weighing between 28 and 31 g, were placed in an anesthesia chamber and transiently anesthetized with isoflurane (Henry Schein). After approximately 5 minutes and in the absence of reflex (toe pinch), mice were bled via retro-orbital sinus at t=0. A volume of 25 μL of whole blood was taken from the retro-orbital sinus and added to 40 μL of saline supplemented with EDTA (0.125%) and sodium metabisulfite (1 mg/mL) (3.85× dilution). Mice (N=3) were then immediately dosed intraperitoneal (IP) injection with dipivefrin chloride formulated as an aqueous solution at 1.06 mg/kg (equivalent to 0.5 mg/kg racemic epinephrine). Following IP administration, mice were then retro-orbital bled under anesthesia at the following time points: 5, 15, 30, 1 h, 2 h, 4 h, and 6 h. About 45 μl of the diluted plasma was recovered and plated.

Figure 2:
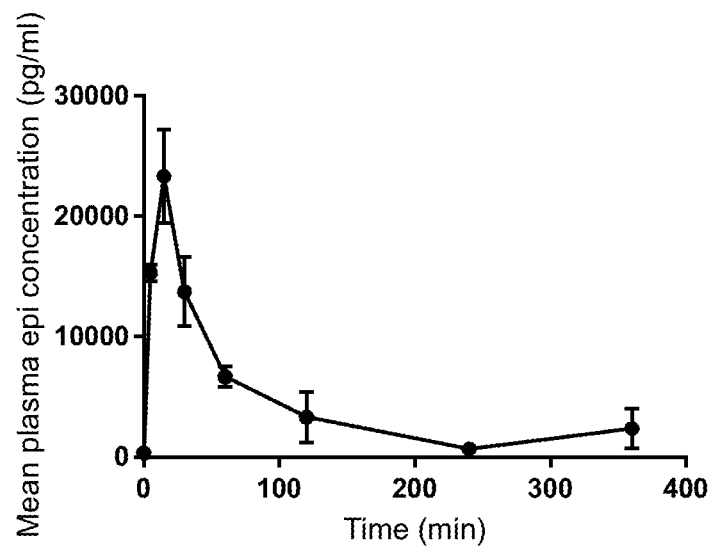
FIG. 2 is a graph of mean plasma epinephrine concentration as a function of time after intraperitoneal (IP) administration of dipivefrin hydrochloride at 1.06 mg/kg (0.96 mg/kg freebase, equivalent to 0.5 mg/ml racemic epinephrine) in mice (N=3).

The plasma samples were analyzed for epinephrine using a validated LC/MS/MS method. FIG. 2 shows mean plasma epinephrine concentration at T0 (pre-dose), 5, 15, 30 min, 1, 2, 4, and 6 h time points. As the data shows, dipivefrin was absorbed rapidly after IP administration and was quickly converted to epinephrine in vivo in minutes.

Example 3. Comparison of Tolerability Between Dipivefrin 0.57 Mg IM (Freebase, Equivalent to 0.3 Mg Racemic Epinephrine) and Epinephrine 0.3 Mg IM The purpose of this example is to demonstrate that dipivefrin is better tolerated than epinephrine when administered via IM injection at the same equivalent epinephrine dose. Six male C57BL6 Mice roughly 14 weeks of age and weighing between 28 and 31 g were placed in an anesthesia chamber and transiently anesthetized with isoflurane (Henry Schein). After approximately 5 minutes and in the absence of reflex (toe pinch), mice were bled via retro-orbital sinus at t=0 (pre-dose). A volume of 25 μL of whole blood was taken from the retro-orbital sinus and added to 40 μL of saline supplemented with EDTA (0.125%) and sodium metabisulfite (1 mg/mL) (3.85× dilution).

Figure 3A:
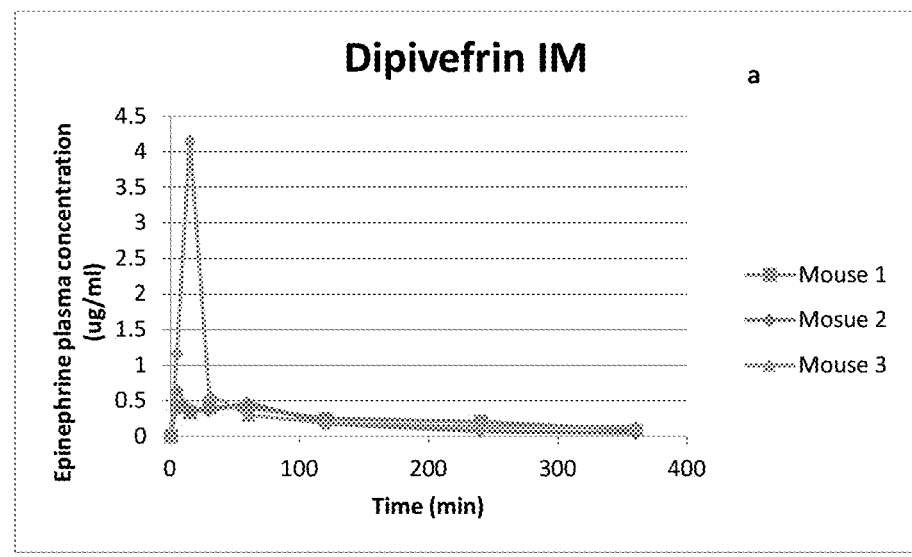
FIG. 3A is a graph of mean plasma epinephrine concentration as a function of time in mice (N=3) after intramuscular (IM) injection with dipivefrin hydrochloride 0.636 mg (0.57 mg freebase, equivalent to 0.3 mg racemic epinephrine).
Figure 3B:
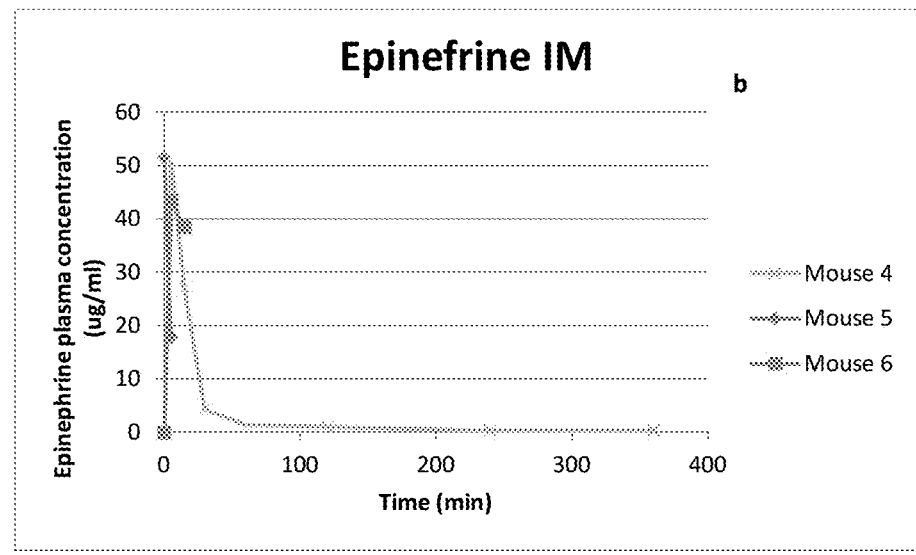
FIG. 3B is a graph of mean plasma epinephrine concentration as a function of time in mice (N=3) after IM injection with epinephrine bitartrate 0.546 mg (0.3 mg freebase).

Three mice were then immediately dosed by intramuscular (IM) injection with dipivefrin hydrochloride 0.636 mg (equivalent to 0.3 mg racemic epinephrine) and three were dosed IM with epinephrine bitartrate 0.546 mg (0.3 mg freebase). Following IM administration, mice were then retro-orbitally bled under anesthesia at the following time points: 5, 15, 30, 1 h, 2 h, 4 h, and 6 h. About 45W of plasma (3.85× dilution, see Example 1 for details) was recovered and plated. The three mice dosed with dipivefrin hydrochloride appeared to be normal throughout the study and showed no signs of distress or illness. The animals dosed with epinephrine bitartrate were cold and lethargic approximately 5 minutes after IM injection. Two out of three mice in this group were found dead approximately 20 minutes post compound administration, with a pinkish fluid coming out of their noses and mouths. Plasma epinephrine concentration vs time profiles for the dipivefrin hydrochloride and epinephrine bitartrate groups are shown in FIGS. 3A and 3B, respectively. As the data in FIG. 3A show, dipivefrin hydrochloride was absorbed rapidly upon IM injection and quickly converted into epinephrine. FIG. 3B shows that IM injection of epinephrine at the same equivalent dose of 0.3 mg caused ca 10-100 fold higher epinephrine concentration in plasma than dipivefrin ($C_{max}$) which would explain the acute toxicity of epinephrine IM. This example illustrates the danger of potential accidental overdosing of epinephrine administered by IM injection as a result of the rapid rise in epinephrine in blood to a lethal level. On the other hand, the safety risk of overdosing by IM administration of dipivefrin is greatly diminished since the conversion to epinephrine is regulated by availability of the enzymes that are responsible for the conversion of the prodrug to epinephrine. Thus we believe dipivefrin is a safer source for epinephrine when given by injection than direct injection of epinephrine, given the potential risks of overdosing with direct epinephrine injection.

Example 4. Evaluation of Dipivefrin Activity as a Single Agent in the Treatment of Subcutaneous B16-F10 Syngeneic Melanoma Tumors at Both Tumor Induction and Tumor Development Stages in C57BL/6J Mice This preclinical study evaluates in vivo therapeutic activity of dipivefrin 15.3 mg/kg (freebase, equivalent to 8 mg/kg racemic epinephrine) administered orally as a single agent in the treatment of subcutaneous B16-F10 syngeneic melanoma tumors at both tumor induction and tumor development stages in C57BL/6J mice. The experimental design of the study is summarized in Table 2.

TABLE 2

| | Days | | | | | | | | |
|---|---|---|---|---|---|---|---|---|---|
| | Day (−7) (Daily Dosing starts) | Day 0 (B16-F10 s.c. lower flank injection 2 × 10⁵ cells in 0.1 mL PBS) | Day 3 | Day 8 | Day 10 | Day 12 | Day 14 | Day 17 | Day 19 |
| Vehicle control (N = 20) | X | X | X | X, Y | X | X | X | X | X, Z Control (N = 10) Group 1a |
| | | | | X | X | X | X | X | X, Z Drug (N = 10) Group 1b |
| Study drug (N = 10) | X | X | X | X | X | X | X | X | X, Z Group 2 |

Note:
X = body weight, clinical observations, tumor size (after induction only, determined by macroscopic caliper measures).
Y = At day 8 (8th day after tumor inoculation), after performing X, the animals were randomly assigned to two equal groups, and one group continued to receive daily vehicle and the other started to receive daily drug starting at day 8.
Z = Animals were sacrificed after performing X
Action Y was performed on day 8 post cell inoculation.

The treatments were started 7 days before tumor inoculation per study design (day −7). The test article administration and the number of animals in each study group are shown in Table 3.

TABLE 3

| Group | N | Treatment | Dose (freebase, mg/kg) | Dosing Route | Schedule |
|---|---|---|---|---|---|
| 1a | 10 | Vehicle | 0 | Per oral (p.o.) | Once a day (QD) × 26 from day −7 to day 18 |
| 1b | 10 | Dipivefrin | 15.3 | p.o. | QD × 11 from day 8 to day 18 |
| 2 | 10 | Dipivefrin | 15.3 | p.o. | QD × 26 from day −7 to day 18 |

Note:
N: animal number;
For group 1a and 1b, dosing was initiated on the day of second randomization (Second randomization was performed on day 8). For group 2, dosing was initiated on the day of cell inoculation. Dosing volume: adjust dosing volume based on body weight (8 µl/g).

The endpoints of the study included the following: tumor growth inhibition (TGI); reduction in median tumor volume on a given day; survival of all animals will be followed and Median Survival Time (MST) and increase in life-span (ILS) will be calculated for each group.

The percent tumor growth inhibition (TGI %) is an indication of antitumor effectiveness, and is expressed as: TGI (%)=100×(1−T/C), in which T and C are the mean tumor volume of the treated and control groups, respectively, on a given day.

The endpoint for each mouse is either a tumor volume>3000 mm³ or the animal is in extreme discomfort (such as pain, seizure, difficulty breathing, etc.). The increase in life-span (ILS) is calculated as follows: ILS (%)=100×[(Median Survival Time of drug treated group/Median Survival Time of vehicle group)−1](%)

Female C57BL/6J mice (Shanghai Lingchang Bio-Technology Co. Ltd (LC, Shanghai, China; Animal Certificate No.: 2013001825675) were used in the study. At inoculation, mice were 7-8 weeks old with a body weight of 16.2-18.6 g. The mice were kept in an Individually Ventilated Cage (IVC) system at constant temperature (22~24° C.) and humidity (60-70%) with 5 animals in each cage Animals had free access during the entire study period to a standard mouse diet (a $Co^{60}$ irradiation-sterilized dry granule food) and water.

The test articles used in the study were dipivefrin hydrochloride (1.9 mg/ml freebase, pre-formulated dosing solution) or the vehicle (purified water containing 0.005% wt of benzalkonium chloride as preservative). Each was stored at 4° C. The B16-F10 tumor cells were maintained in vitro as a monolayer culture in DMEM medium supplemented with 10% fetal bovine serum at 37° C. in an atmosphere of 5% $CO_2$ in air. The tumor cells were routinely subcultured twice per week. The cells growing in an exponential growth phase were harvested and counted for tumor inoculation.

Each mouse was inoculated subcutaneously at the right flank region with $2 \times 10^5$ B16F10 tumor cells in 0.1 ml of PBS for tumor development. The treatments were started 7 days prior to the inoculation. The test article was administered to the tumor-bearing mice according to the predetermined regimen as shown in the Study Design Table 3. The date of tumor cell inoculation was denoted as day 0.

First Grouping:

On day 7, all 30 animals were weighed and the body weight was used as numeric parameter to randomize selected animals into two groups in an effort to minimize systematic error. Dosing was administrated as indicated in Table 4.

TABLE 4

First Grouping

| Group | N | Treatment | Dose (freebase, mg/kg) | Dosing Route | Schedule |
|---|---|---|---|---|---|
| 1 | 20 | Vehicle | 0 | p.o. | QD × 15 (from day −7 to day 7) |
| 2 | 10 | Dipivefrin | 15.3 | p.o. | QD × 15 (from day −7 to day 7) |

Note:
N: animal number.

Second Grouping:

On day 8, all 20 animals in group-1 were randomized into two groups (1a and 1b) based on tumor volume. Dose administrations were performed as shown Table 5.

TABLE 5

Second Grouping

| Group | N | Treatment | Dose (freebase, mg/kg) | Dosing Route | Schedule |
|---|---|---|---|---|---|
| 1a | 10 | Vehicle | 0 | p.o. | QD × 11 (from day 8 to day 18) |
| 1b | 10 | Dipivefrin | 15.3 | p.o. | QD × 11 (from day 8 to day 18) |

TABLE 5-continued

Second Grouping

| Group | N | Treatment | Dose (freebase, mg/kg) | Dosing Route | Schedule |
|---|---|---|---|---|---|
| 2 | 10 | Dipivefrin | 15.3 | p.o. | QD × 11 (from day 8 to day 18) |

Both randomization procedures were performed using STUDYDIRECTOR™ software (Studylog Systems, Inc. CA, USA). One optimal randomization design (generated by the Matched Distribution Method) that showed minimal group to group variation in body weight or tumor volume was selected for group allocation.

Treatment was initiated 7 days before inoculation per study design (Table 2).

After tumor cell inoculation, animals were checked daily for morbidity and mortality. At the time of routine monitoring, the animals were checked for any effects of tumor growth and treatments on normal behavior such as mobility, food and water consumption, body weight gain/loss (body weights were measured twice or thrice per week), eye/hair matting and any other abnormal effect. Death and observed clinical signs were recorded on the basis of the numbers of animals within each subset.

Tumor volumes were measured twice or thrice per week in two dimensions using a caliper, with the volume in $mm^3$ estimated using the formula: $V=0.5 \, a \times b^2$ where a and b are the long and short perpendicular diameters of the tumor, respectively. The procedures of dosing as well as tumor and body weight measurement were conducted in a Laminar Flow Cabinet.

On day 17, mice which tumor volumes exceeded 3000 $mm^3$ were euthanized and the whole study was terminated on day 19. Additionally, mouse #15 in group 1-b was dead on day 13 due to an operation error, while mouse #7 in group 1-a was found dead on day 18 due to tumor ulceration.

Statistical analysis of the difference in tumor volume among the groups was conducted on the data obtained at day 5, day 14, and day 19 after tumor inoculation using Independent-Samples T Test or Mood's Median Test.

The survival time was analyzed by Kaplan-Meier method. The event of interest was the endpoint of individual tumor volume reached 3000 $mm^3$ or animal death. The survival time was defined as the time from the day post tumor cell inoculation to the day of animal death or euthanized. For each group, the median survival time (MST), corresponding 95% confidence interval and the increased in life-span (ILS) were calculated. The Kaplan-Meier curves were also constructed for each group and the log-rank test was used to compare survival curves between groups.

All data were analyzed in SPSS (Statistical Product and Service Solutions) version 18.0 (IBM, Armonk, N.Y., U.S.) or GRAPHPAD PRISM 5.0. P-values were rounded to three decimal places, with the exception that raw P-values less than 0.001 were stated as P<0.001. All tests were two-sided. P<0.05 was considered to be statistically significant.

Figure 4:
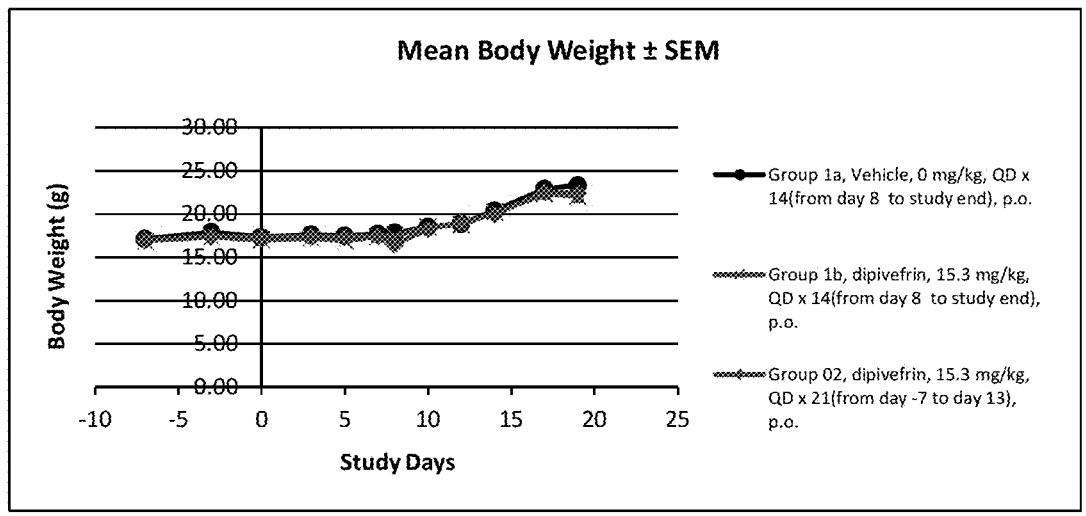
FIG. 4 is a graph of mean body weight of mice of all treatment groups as a function of study day.

No body weight differences were observed among the treatment groups during the treatments of both tumor induction and development (See FIG. 4) and no drug related deaths were observed during the study period. Thus administration of dipivefrin hydrochloride daily at 15.3 mg/kg (freebase) has no effect on body weight.

Figure 5:
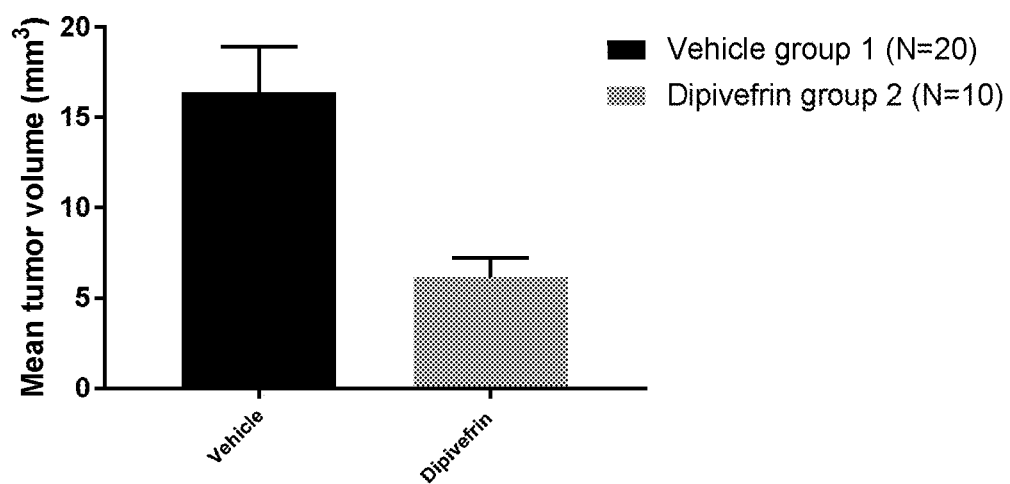
FIG. 5 is a bar chart showing mean B16F10 tumor volume 5 days after tumor cell inoculation of the mice.

Oral administration of dipivefrin was also shown to significantly inhibit B16F10 tumor formation after tumor cell inoculation. FIG. 5 shows mean tumor volumes of the dipivefrin- and vehicle-treated mice 5 days post-B16F10 cancer cell inoculation. As the data show, dipivefrin hydrochloride-treated mice showed significantly smaller tumor volume than the vehicle-treated mice (6.2±1.1 mm$^3$ vs 16.4±2.5 mm$^3$, p<0.01, independent t-test) during the early stage of tumor induction. This observation suggests that dipivefrin induced killing of cancer cells at the inoculation site.

Figure 6:
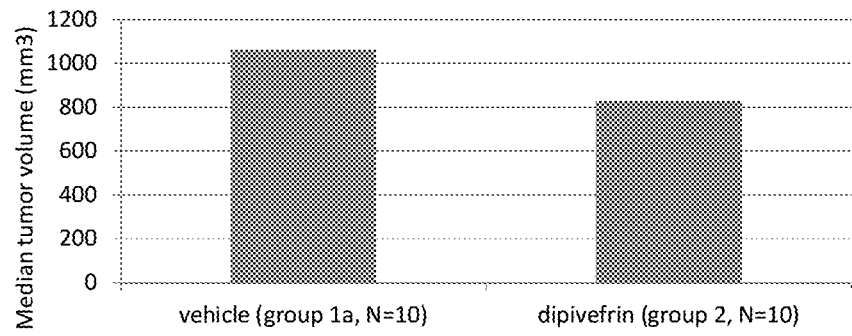
FIG. 6 is a bar chart showing median B16F10 tumor volume 14 days post-tumor cell inoculation of the mice.

Oral administration of dipivefrin also resulted in significant reduction in median tumor volume, compared to vehicle, 14 days post B16F10 tumor cell inoculation of the mice. Shown in FIG. 6 are median tumor volumes of the dipivefrin- and vehicle-treated mice 14 days post B16F10 cancer cell inoculation. As the data show, dipivefrin treated mice showed significantly smaller median tumor volume than the vehicle treated mice (827 mm$^3$ vs 1060 mm$^3$, p<0.05, Mood's median test).

Figure 7:
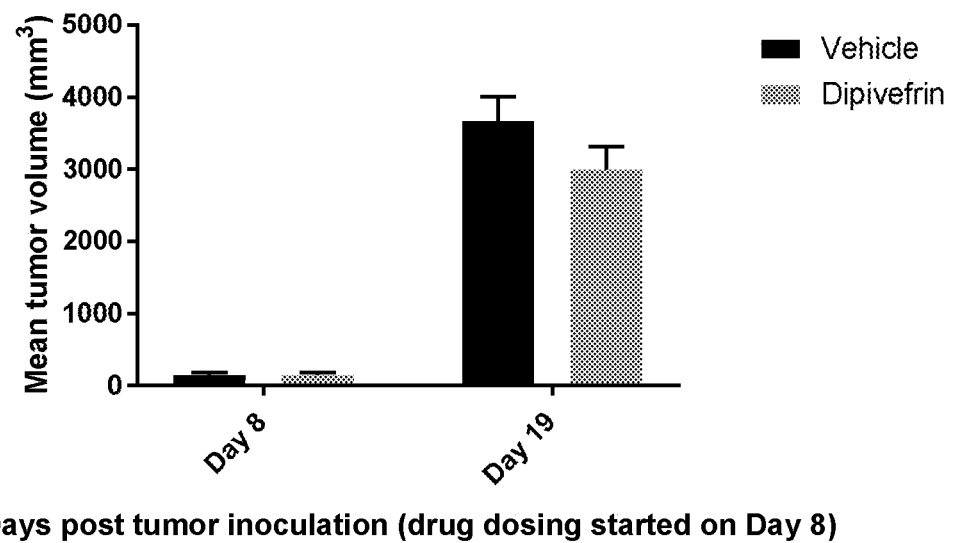
FIG. 7 is a bar chart showing mean tumor B16F10 volume for dipivefrin vs vehicle treatment after the tumor was established.

Oral administration of dipivefrin was also shown to inhibit B16F10 tumor growth after the tumor has been established. The vehicle-treated mice (group 1, N=20) were randomized into two equal groups of 10 each (1a and 1b) 8 days after B16F10 tumor inoculation based on the tumor volume (mean tumor volume 145.5±30.8 mm$^3$ for group 1a vs 145.6±35.6 mm$^3$ for group 1b). While the group 1a mice continued to receive vehicle, the group 1b mice received daily oral dipivefrin starting from day 8. At day 19, the dipivefrin treated group had about 18% reduction in mean tumor volume compared to the vehicle treated group (2997.2±341.6 mm$^3$ vs 3668.0±311.9 mm$^3$) The data are also shown in FIG. 7.

Figure 8:
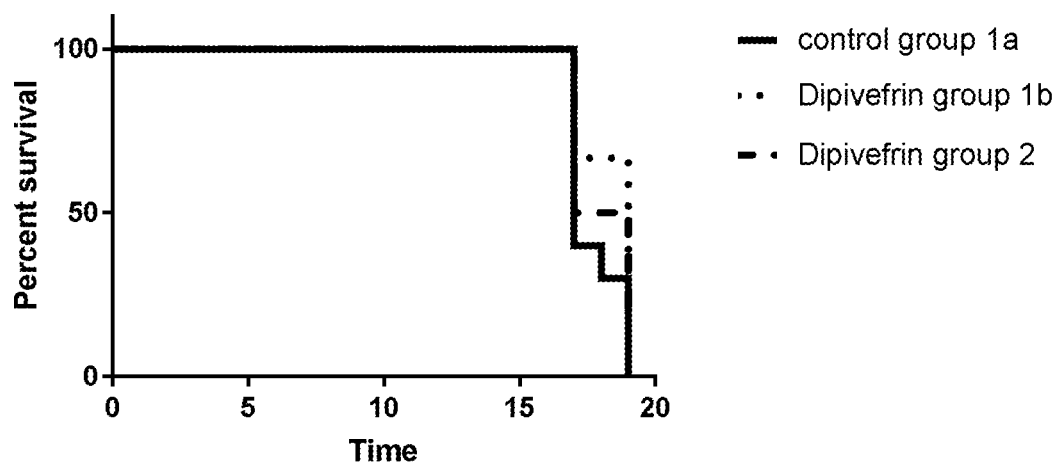
FIG. 8 is a graph showing percent survival as a function of study time (Kaplan-Meier curves) for groups 1a, 1b and 2.

Oral administration of dipivefrin significantly extended survival time compared to vehicle in the treatment of subcutaneous B16F10 tumors in C57BL/6J mice. The survival times of different groups are shown in Table 6. The Kaplan-Meier survival curves of these groups are shown in FIG. 8. The log-rank test was used to compare survival curves between groups. The dipivefrin treated group 1b demonstrated significant increase in life-span (ILS) compared to the vehicle treated group 1a (12%, p=0.038). The dipivefrin treated group 2 showed 6% increase in life-span compared to vehicle. While this increase in life-span did not reach statistical significance (p=0.175), it lends support to the fact that dipivefrin provides survival benefits as compared to vehicle. The survival times of the two dipivefrin treated groups 1a and 2 are not statistically different as expected (p=0.448).

TABLE 6

Antitumor Activity of dipivefrin in the Treatment of Subcutaneous B16F10 tumors in C57BL/6J Mice by Survival Time Analysis

| Treatment | MST (days) | 95% Confidence Interval (days) | ILS (%) | P value |
|---|---|---|---|---|
| Group-1a Vehicle | 17.0 | 17.0-18.2 | — | — |
| Group-1b dipivefrin (15.3 mg/kg) | 19.0 | 17.7-19.0 | 12% | 0.038[1] |
| Group-2 dipivefrin (15.3 mg/kg) | 18.0 | 17.3-18.7 | 6% | 0.175[2] |

[1]vs. vehicle control;
[2]group-1b vs. group-2, p = 0.448.

Example 5. Efficacy of Dipivefrin for Treatment of Influenza A(H1N1pdm) Virus Infection in C57BL/6 Mice These experiments demonstrate that oral treatment of mice with dipivefrin can help prevent death and reduce body weight loss due to influenza. The effect of dipivefrin on A/California/04/2009 (H1N1pdm) virus infection was tested in C57BL/6J mice.

Twelve female C57BL/6J mice from Jackson Laboratories (Bar Harbor, Me., 18-20 g) were anesthetized by i.p. injection of ketamine/xylazine (50/5 mg/kg) followed by intranasal (i.n.) exposure to a 75-μL suspension of influenza virus. The infectious inoculum of virus is a 90% lethal challenge dose based on results from a previous mouse titration study. Six mice was administered dipivefrin HCl (0.16 ml, formulated as 1.06 mg/ml solution equivalent to 0.5 mg/mL epinephrine) p.o. one time 24 hours after infection at a dose of 8.48 mg/kg (equivalent to 4 mg/kg epinephrine). A placebo (compound vehicle only) was administered in the same dosing regimen to the other six mice. Three mice each from the treated and the placebo group were euthanized on day 3 and day 6 post-infection (p.i.) and lung tissue was harvested. Tissue was weighed and given a hemorrhage score from 0 (unaffected) to 4 (all four lobes—or entire lung—appeared discolored/darkened). Lungs were weighed and frozen at −80° C.

Lung tissue was thawed and homogenized in 1 mL of cell culture medium and titers were performed on homogenate by end-point dilution (10-fold dilutions) in 96-well microplates seeded with confluent MDCK cells. Culture media was MEM with 10 IU/mL porcine trypsin, 1 μg/mL EDTA, and 50 μg/mL gentamicin. Plates were incubated at 37° C. for 5 days then read for viral cytopathic effect in each well. Fifty percent cell culture infectious dose (CCID50) from each lung was determined using the Reed-Muench equation.

Statistical analysis of the data: Individual body weight percentages of day 0 weights were calculated. Mouse weight and lung virus titer statistics were performed using two-way ANOVA followed by Bonferroni's multiple comparisons post-test. Statistical comparisons were made between treated and placebo groups. All statistical analyses were performed using Prism 7.0 (GraphPad Software, San Diego, Calif.).

Figure 10:
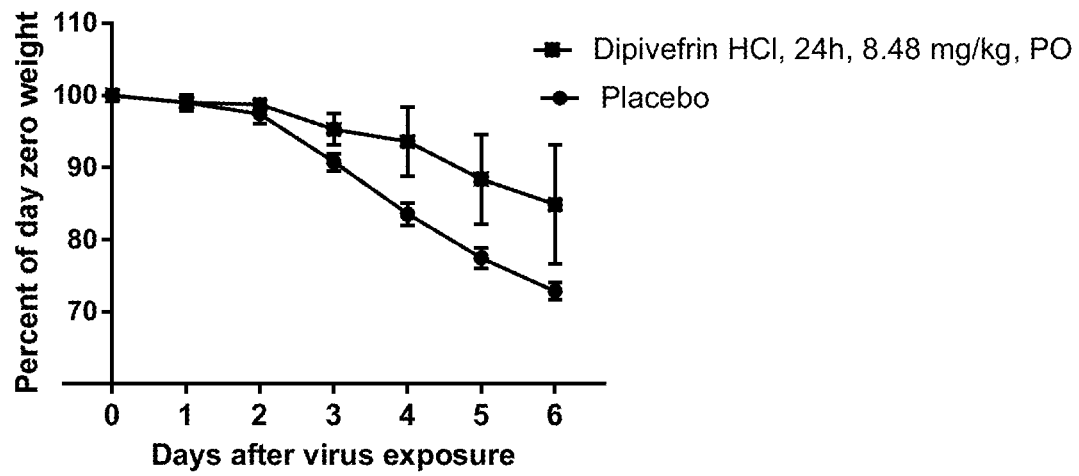
FIG. 10. Effect of single oral dose of dipivefrin HCl on mouse body weight during influenza A/California/04/2009 H1N1pdm virus infection in C57BL/6J mice. One dose of dipivefrin HCl was administered p.o. 24 hours after virus exposure at 8.48 mg/kg. Graph depicts mean weight by percent of initial (day 0) body weight±SEM. *p<0.05.

Body weight changes during the infection are shown graphically in FIG. 10. Mouse body weights differed significantly between the placebo and treatment groups on days 5 and 6 p.i. (p<0.05), with dipivefrin-treated mice losing less weight during the 6-day observation.

Figure 11:
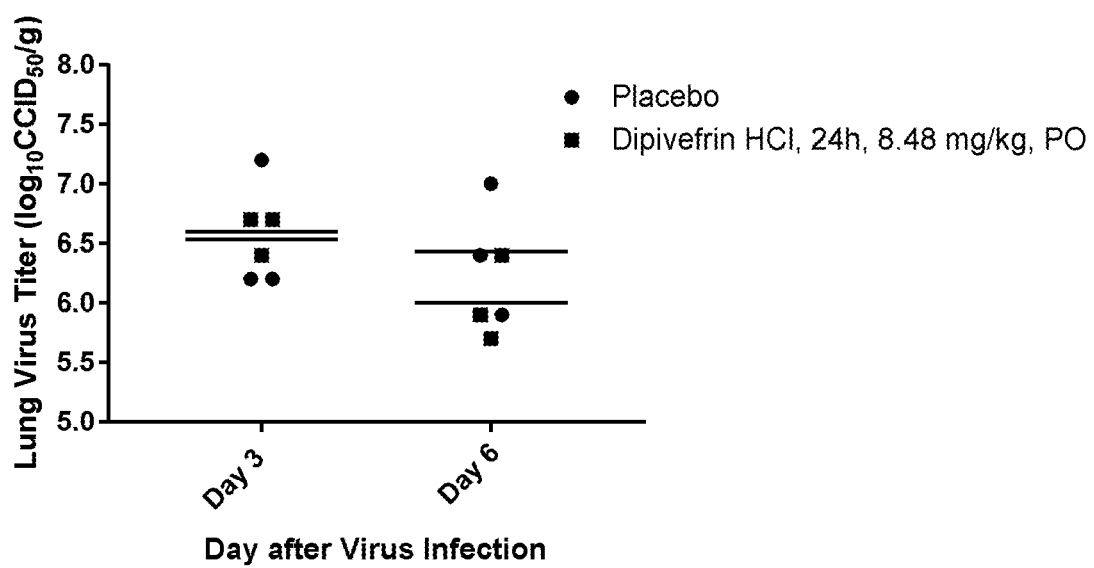
FIG. 11. Effect of single oral dose of dipivefrin HCl on lung viral titers during influenza A/California/04/2009 H1N1pdm virus infection in C57BL/6J mice. A single dose (8.48 mg/kg) of dipivefrin HCl was administered p.o. 24 hours after virus exposure. Lung tissue was harvested from 3 mice from each treatment group on day 3 and day 6 post-inoculation and influenza virus titers determined by end-point titration.

Visual lung hemorrhage scores ranged from 0-3 in both treatment groups. Influenza virus titers in lung tissues did not differ significantly between the treated and placebo groups on day 3 or 6 p.i. (FIG. 11). The drug treated group had lower virus titers in lung tissues on day 6 p.i. than on day 3 p.i (p<0.05). The lung virus titers did not differ significantly between these two days p.i. for the placebo group (p=0.42). Of note, one treated mouse maintained its body weight during the challenge period, despite having lung virus titers on day 6 p.i.

In summary, in this study, mice were treated with a single dose of 8.48 mg/kg dipivefrin HCl 24 hours after virus challenge. Treated mice were less ill as demonstrated by less weight loss compared to placebos (p<0.05). The average lung virus titers on day 6 were slightly lower in treated mice compared to placebos, the difference was not statistically significant. The drug treated group had significantly lower virus titers in lung tissues on day 6 p i than on day 3 p.i. (p<0.05). The lung virus titers did not differ significantly between these two days p.i. for the placebo group (p=0.42). Of note, one treated mouse maintained its body weight during the challenge period, despite having lung virus titers on day 6 p.i.

Example 6. Antibacterial Activity of Dipivefrin in a Peritonitis-Sepsis Model of MRSA Infection This example demonstrates in vivo antibacterial activity of dipivefrin.

Figure 9:
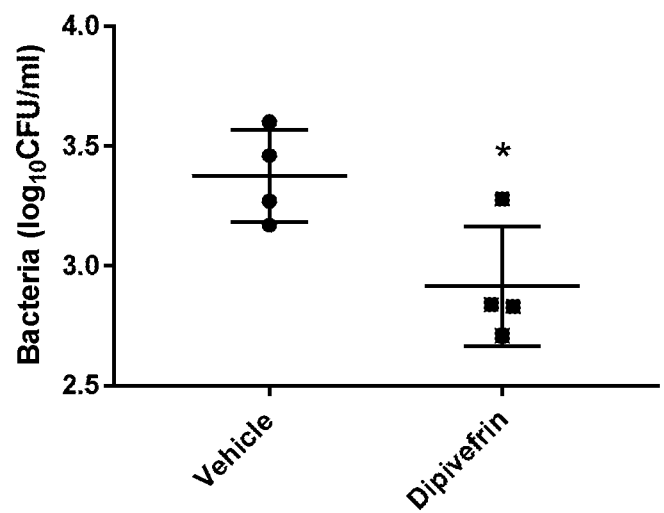
FIG. 9 is a graph showing blood bacterial levels 4 hours post MRSA infection.

Two (2) groups of C57BL/6J 6 to 8 week old female mice (ca 20 g body weight) with 10 mice/group were injected IP with $2\times10^8$ CFU/mL of methicillin-resistant *Staphylococcus aureus* (MRSA) NRS71-Sanger 252 in a volume of 200 μL. The treatment group was dosed with dipivefrin 15.3 mg/kg (freebase) by oral gavage starting at t=−5 days relative to bacterial inoculation. Dosing occurred once daily up to 7 days post bacterial inoculation. Body weights were measured once per day on days 0 to 7 and the experimental endpoint was survival at 7 days Animals falling below 20% of original weight post-infection was euthanized. Four hours (4 hours) post infection, blood was drawn from 4 animals in each group and bacterial load was determined through a standard plating assay. Each blood sample was diluted by serial log dilutions and 10 dilutions ($10^0$ to $10^{-9}$) was plated in duplicate on TSA with 5% sheep's blood. The plates were incubated for 24 hours at 37° C. at which time formed colonies was enumerated and CFU/mL was determined. One mouse in the vehicle group was found dead the next day following infection and no subsequent death occurred up to 7 days post infection. No mouse died in the treatment group up to 7 days post infection. The blood bacterial counts 4 hours post infection were significantly higher for the vehicle treated group than the drug treated group (p<0.05, two-tailed, unpaired t-test, FIG. 9).

Example 7. Preparation of Dipivefrin Hydrochloride Orally Dissolving Tablets

Gelatin (100 mg) was first dissolved in deionized water (5.0 g) at 40° C. to obtain a clear solution. Other inactive ingredients listed in Table 7 were then added and dissolved in the gelatin solution at room temperature. Dipivefrin hydrochloride (635.2 mg) was added and dissolved last to obtain the drug solution which was dispensed into blister pockets (593.5 mg/pocket) using a pipette. The filled blister pack was placed on dry ice for 2 h and transferred into a freeze drying flask which was attached to a manifold freeze dryer and lyophilized for 24 h. The tablets thus obtained containing 63.5 mg of dipivefrin HCl per tablet can be readily removed from the blister pack and stored in a glass bottle. The tablets were inspected for surface smoothness/elegance and brittleness. The dipivefrin HCl orally dissolving 5 mg tablets were prepared in the same fashion except 535 mg of the drug solution was dispensed into each blister pocket.

In Vitro Dissolution Testing.

One tablet was carefully dropped into 2 ml of gently-stirred simulated saliva pre-heated to 37° C. Time to complete dissolution of the tablet was recorded using a smart phone timer.

In Vivo Dissolution/Taste Testing.

One tablet was placed on the tongue of a healthy adult male volunteer. Month was held closed without chewing or swallowing. Time to complete dissolution of the tablet was recorded using a smart phone timer. Afterwards, the subject's mouth was inspected for any sign of undissolved tablet residue. The volunteer was then asked to describe taste, mouth feel and possible irritation.

TABLE 7

| Ingredient | Dipivefrin HCl orally dissolving tablet, 63.5 mg Amount (mg) | Dipivefrin HCl orally dissolving tablet, 5 mg Amount (mg) |
|---|---|---|
| dipivefrin HCl | 635.2 | 50 |
| Gelatin | 100 | 100 |
| D-Mannitol | 50 | 50 |
| Glycine | 50 | 50 |
| PVPK30 | 50 | 50 |
| Citric acid | 25 | 25 |
| Sucralose | 25 | 25 |
| DI water | 5000 | 5000 |
| Total | 5935.2 | 5350 |
| # of Tablets | 10 | 10 |
| Tablet strength (mg) | 63.5 | 5 |
| Surface smoothness | Good | Good |
| Strength | Good | Good |
| in vitro disintegration time | <10 seconds | 4.9 seconds |
| In vivo disintegration time | Not determined | <3 seconds |
| Bitterness | No | No |
| Tongue irritation | Some tongue burning sensation | Not detected |

Example 8. Pharmacokinetic Studies of Dipivefrin after Single Oral Administration in Rabbits Female New Zealand White Rabbits aged 3.2 months and ranging from 3.4 to 3.6 kilograms in weight at study initiation were utilized for this study Animals were identified by ear tags and cage labels. The animals were healthy at the start of the study. The animals were housed one per cage within the same room. Primary enclosures were as specified in the USDA Animal Welfare Act (9 CFR, Parts 1, 2, and 3) and as described in the Guide for Care and Use of Laboratory Animals (ILAR publication, 2011, National Academy Press) Animals were fed a certified laboratory diet (Certified Rabbit Diet HF 5325). Water was supplied ad libitum to the animals. Two groups of animals were administered PO dipivefrin HCl formulated as 2.12 mg/ml solution (equivalent to 1 mg/ml racemic epinephrine freebase) in purified water via rubber oral gavage tube followed by a 5 mL flush with water. A third group of animals were administered PO dipivefrin HCl formulated as orally dissolving tablet. The animals were manually restrained using cloth restrainers. Dosing occurred at 0 hours on the appropriate day in accordance with the Study Design shown in Table 8.

TABLE 8

Study Design (non-crossover)

| Group # | Test Article | Dosing Route | N= | Dose | Vehicle flush | Plasma Sampling Time Points |
|---|---|---|---|---|---|---|
| 1 | Dipivefrin HCl 21.2 mg/ml solution | PO, oral gavage | 4 | 0.3 ml/ animal | Water, 5 ml | Pre-dose, 5, 10, 15, 30, 40 min, 1 hr, and 1.5 hr |
| 2 | | PO, oral gavage | 3 | 3 ml/ animal | Water, 5 ml | Pre-dose, 5, 10, 15, 30, 40 min, 1 hr, and 1.5 hr |

TABLE 8-continued

Study Design (non-crossover)

| Group # | Test Article | Dosing Route | N= Dose | Vehicle flush | Plasma Sampling Time Points |
|---|---|---|---|---|---|
| 3 | Dipivefrin HCl orally dissolving tablet, 63.5 mg | Orally dissolving tablet | 4 | 1 tablet/ animal | none | Pre-dose, 5, 10, 15, 30, 40 min, 1 hr, and 1.5 hr |
| 4 | Epinephrine | IM | 4 | 0.3 mg/ animal | N/A | Pre-dose, 5, 10, 15, 20, 30, 40, 60, and 80 min |

Whole blood samples (~0.5 to 1 mL) were collected from the animal's ear vessel via direct venipuncture at the appropriate time point and placed into K2EDTA tubes as the anticoagulant. Blood samples were centrifuged at a temperature of 4° C. at 3000 g for 5 minutes. All samples were maintained chilled throughout processing. Plasma samples (250 μL) were aliquoted into 50 uL of 6% wt sodium metabisulfite solution in an eppendorf tube, and placed in a freezer set to maintain ~−70° C. until shipment in dry ice to the Keystone Bioanalytical for analysis of plasma concentrations of epinephrine.

The PK analysis results are summarized in Table 9.

TABLE 9

| Test articles | Route of administration | Dose | $C_{max}$ (ng/ml) | $T_{max}$ (min) | $AUC_{last}$ (ng min/ml) |
|---|---|---|---|---|---|
| Dipivefrin HCl orally dissolving tablet | Orally dissolving tablet | 63.5 mg | 28.01 ± 5.21 | 75.0 ± 15 | 1283.46 ± 203.82 |
| Dipivefrin HCl oral solution | Oral gavage | 63.6 mg | 2.25 ± 0.52 | 51.7 ± 24.9 | 99.25 ± 31.44 |
| Dipivefrin HCl oral solution | Oral gavage | 6.36 mg | 0.66 ± 0.29 | 32.5 ± 10.9 | 24.40 ± 7.18 |
| Epinephrine | IM | 0.3 mg | 50.23 ± 14.95 | 10.0 ± 2.9 | 1174.10 ± 85.49 |

$C_{max}$: maximum plasma concentration (mean±SEM of individual rabbit Cmax values); $T_{max}$: time at which maximum plasma epinephrine concentration was achieved (mean±SEM of individual rabbit $T_{max}$ values); $AUC_{0-last}$: area under the plasma concentration versus time curve (mean±SEM of individual rabbit AUC values). $T_{max}$ is the time at which the highest peak epinephrine concentration occurred in each individual rabbit. $T_{max}$ is limited by experimental design because it is a discrete variable based on defined times of blood sampling.

Figure 12:
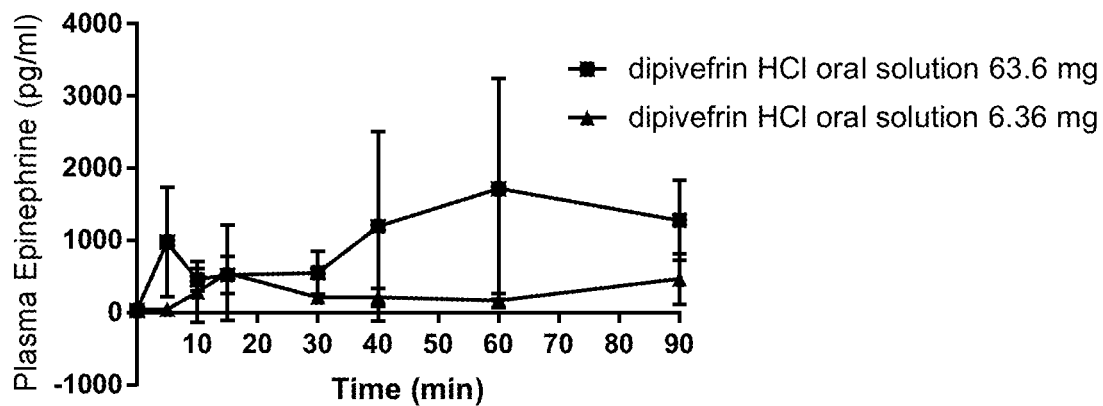
FIG. 12. Mean plasma epinephrine concentration vs time profiles after single oral dose of dipivefrin HCl oral solution 63.6 mg and dipivefrin HCl oral solution 6.36 mg in rabbits.
Figure 13:
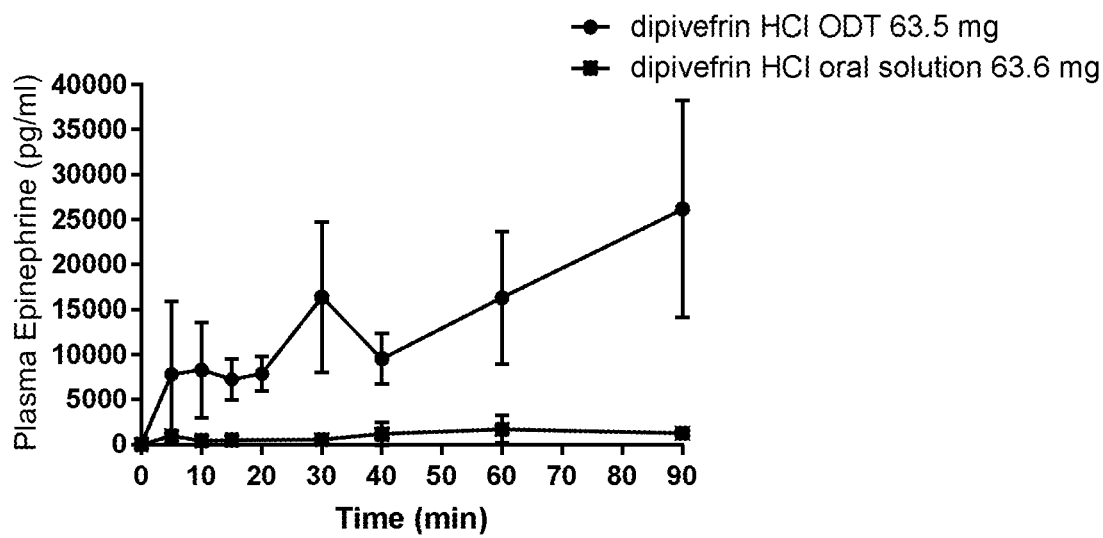
FIG. 13. Mean plasma epinephrine concentration vs time profiles after single oral dose of dipivefrin HCl orally dissolving tablet 63.5 mg and dipivefrin HCl oral solution 63.6 mg in rabbits.
Figure 14:
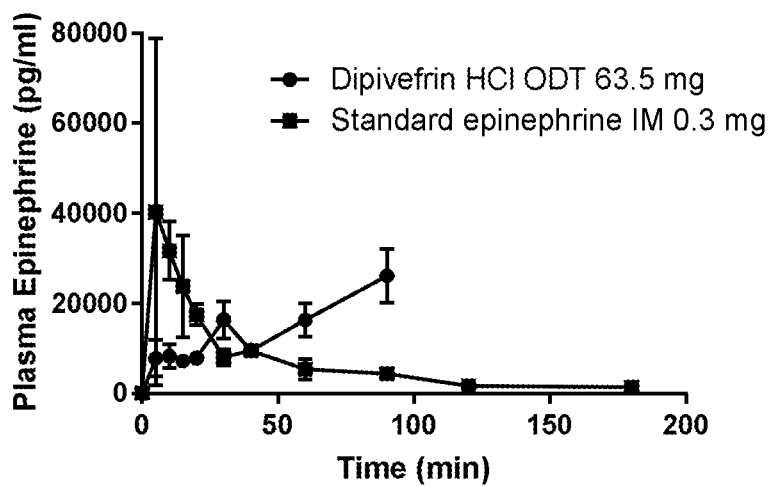
FIG. 14. Mean plasma epinephrine concentration vs time profiles after single oral dose of dipivefrin HCl orally dissolving tablet 63.5 mg and epinephrine IM injection 0.3 mg in rabbits.

The mean plasma epinephrine concentration vs time profiles are shown in FIGS. 12-14. This example demonstrates the following: (a) bioavailability of epinephrine increases with dose of dipivefrin HCl after oral administration; (b) at the same dose, dipivefrin HCl orally dissolving tablet provides much higher bioavailability of epinephrine than dipivefrin HCl oral solution administered via oral gavage; (c) compared to the epinephrine IM 0.3 mg, the standard care for anaphylaxis, dipivefrin HCl orally dissolving tablet 63.5 mg appears to release epinephrine into the blood stream over longer period of time resulting in lower $C_{max}$ although comparable overall or even higher AUC in rabbits.

Slow release of epinephrine into the blood stream after oral administration of dipivefrin HCl in rabbits is surprising given the fact that epinephrine is rapidly released when dipivefrin HCl is administered into the rabbit's eye (Anderson, J. A. et al Invest Ophthalmol Vis Sci. 1980, 19:817-23). Butyrylcholinesterase (BChE, EC 3.1.1.8) is thought to play a major role in converting dipivefrin to epinephrine in the rabbit cornea (Nakamura M., et al., Ophthalmic Res 1993; 25:46-51). Low $C_{max}$ and long $T_{max}$ of epinephrine after oral administration of dipivefrin HCl would have made it unsuitable as an oral therapy for emergency treatment of anaphylaxis. In an anaphylactic episode, prompt release of epinephrine is essential.

Without wishing to be bound by theory, the inventor had hypothesized that the slow release of epinephrine after oral administration of dipivefrin HCl in rabbits could be caused by the relatively low butyrylcholinesterase (BChE, EC 3.1.1.8) activity in rabbit plasma. Because the predominant cholinesterase in rabbit plasma is acetylcholinesterase (AChE; EC 3.1.1.7) as reported by Oropesa A. L., et al (Ecotoxicol Environ Saf 2014, 100:39-43), rabbits are not appropriate PK model for oral dipivefrin HCl.

Example 9. Pharmacokinetic Studies of Dipivefrin after Single Oral Administration in Dogs Pharmacokinetics of dipivefrin HCl was evaluated in dogs in a three leg cross-over design according to Table 10 below. Four days prior to study initiation, 1 mL of whole blood was collected from four (n=4) non-naïve male Beagle dogs, aged 1.5-6.5 years and ranging from 9.8 to 10.8 kilograms in weight, into 4 chilled tubes containing K2EDTA. The blood was processed to plasma and plasma cholinesterase activity was assayed according to the Ellman method using acetylthiocholine iodide as the substrate (Ellman, G. L. et al Biochemical Pharmacology, 1961, volume 7, page 88-95). The assay results are summarized in Table 10. Based on the plasma cholinesterase activity assay results, the first three dogs with highest plasma cholinesterase activity were selected for the PK study.

TABLE 10

| dog # | Plasma cholinesterase activity (U/L) |
|---|---|
| 1 | 1408.3 |
| 2 | 1389.2 |
| 3 | 1441.4 |
| 4 | 1125.4 |

The dogs were housed one per cage and identified by ear tags and cage labels. The animals were healthy at the start of the study. Primary enclosures were as specified in the USDA Animal Welfare Act (9 CFR, Parts 1, 2, and 3) and as described in the Guide for Care and Use of Laboratory Animals (ILAR publication, 2011, National Academy Press) Animals were fasted for a minimum of 12 hours prior to dosing and returned 4 hours post dose; Water was supplied ad libitum to the animals.

Dosing occurred at 0 hours on the appropriate day in accordance with the Study Design table (Table 11). The first leg of epinephrine IM 0.3 mg, standard care for anaphylaxis, is included as a control. The intramuscular dose was administered via 25 gauge needle and syringe into the lateral aspect of the left or right thigh. The dosing site was clipped free of hair and cleaned with alcohol prior to dosing. The orally dissolving tablets were dosed by placing one tablet on the tongue of the dog. The muzzle was gently held closed for 1-2 minutes. After this period, the mouth was opened to observe that the tablet had completely dissolved.

TABLE 11

Study design (crossover).

| Leg # | Test Article Formulation | Dose Route | N = | Dose | Time points |
|---|---|---|---|---|---|
| 1 | Epinephrine solution | IM | 3 | 0.3 mg/animal | Pre-dose, 5, 10, 15, 20, 30, 40 min, 1, 1.5, 2, and 3 hours post dose |
| | | | Minimum 7 Day Washout | | |
| 2 | Dipivefrin HCl orally dissolving tablet, 63.5 mg | Orally dissolving tablet | 3 | 1 tablet/animal | Pre-dose, 5, 10, 15, 20, 30, 40 min, 1, 1.5, 2 and 3 hours post dose |
| | | | Minimum 7 Day Washout | | |
| 3 | Dipivefrin HCl orally dissolving tablet, 5 mg | Orally dissolving tablet | 3 | 1 tablet/animal | Pre-dose, 5, 10, 15, 20, 30, 40 min, 1, 1.5, 2 and 3 hours post dose |

Whole blood samples (~0.5 to 1 mL) were collected from the dog's jugular vein via direct venipuncture at the appropriate time point and placed into K2EDTA tubes as the anticoagulant. Blood samples were centrifuged at a temperature of 4° C. at 3000 g for 5 minutes. All samples were maintained chilled throughout processing. Plasma samples (250 μL) were aliquoted into 50 uL of 6% wt sodium metabisulfite solution in an eppendorf tube, and placed in a freezer set to maintain ~−70° C. until shipment in dry ice to the Keystone Bioanalytical for analysis of plasma concentrations of epinephrine.

$C_{max}$: maximum plasma concentration (mean±SEM of individual dog $C_{max}$ values); $T_{max}$: time at which maximum plasma epinephrine concentration was achieved (mean±SEM of individual dog $T_{max}$ values); $AUC_{0-last}$: area under the plasma concentration versus time curve (mean±SEM of individual dog AUC values). $T_{max}$ is the time at which the highest peak epinephrine concentration occurred in each individual dog. $T_{max}$ is limited by experimental design because it is a discrete variable based on defined times of blood sampling.

The PK analysis results of dipivefrin HCl in dogs were summarized below (Table 12). The statistical analyses were performed using one-way ANOVA followed by Turkey's multiple comparisons test. All statistical analyses were performed using Prism 7.0 (GraphPad Software, San Diego, Calif.).

Figure 15:
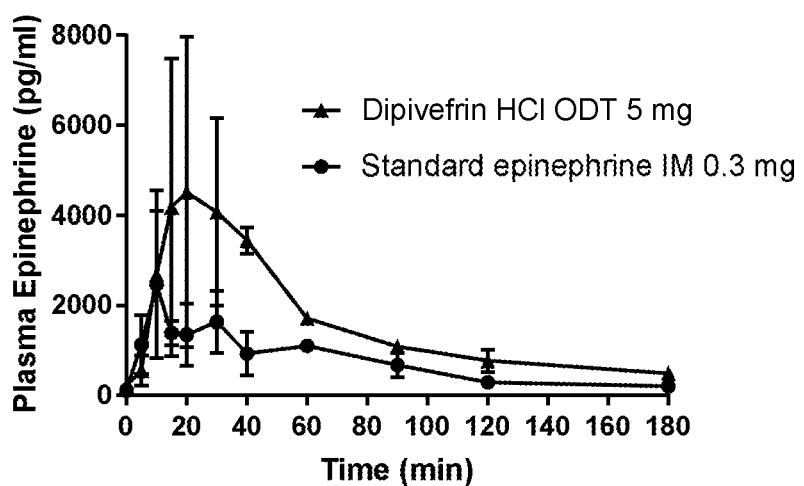
FIG. 15. Mean plasma epinephrine concentration vs time profiles after single oral dose of dipivefrin HCl orally dissolving tablet 5 mg and single standard epinephrine IM injection 0.3 mg in beagle dogs (cross over design, N=3).
Figure 16:
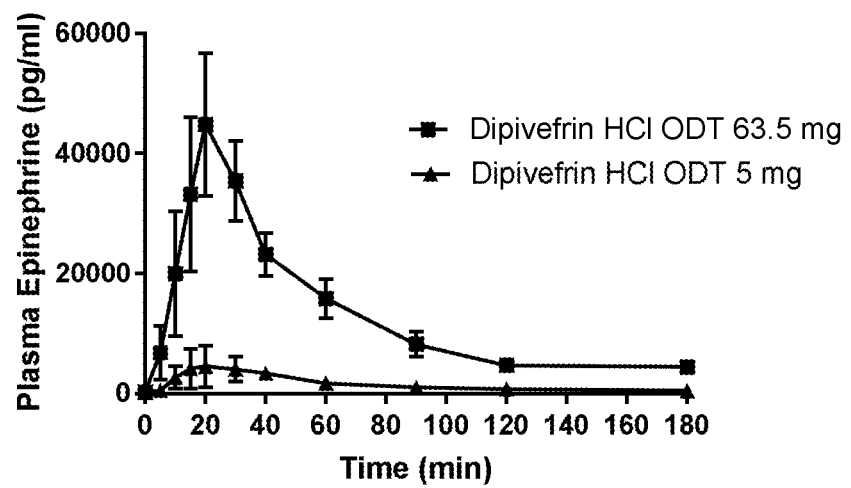
FIG. 16. Mean plasma epinephrine concentration vs time profiles after single oral dose of dipivefrin HCl orally dissolving tablet 5 mg and 63.5 mg in beagle dogs (cross over design, N=3).

After administration of dipivefrin HCl orally dissolving tablet to beagle dogs, plasma epinephrine concentration rises rapidly. The dipivefrin HCl orally dissolving 5 mg tablet dose provided 2 times of $C_{max}$ and $AUC_{last}$ compared to the epinephrine standard IM 0.3 mg injection with comparable $T_{max}$. Dipivefrin HCl 63.6 mg produced significantly higher levels of epinephrine when compared to either the 5 mg dipivefrin HCl orally dissolving tablet ($p<0.05$ for $C_{max}$ and $p<0.01$ for AUC) or the standard epinephrine IM 0.3 mg ($p<0.01$ for both $C_{max}$ and AUC). There is no significant difference in $T_{max}$ among all treatment groups ($p>0.6$). This example demonstrates that a dipivefrin HCl ODT can produce statistically equivalent levels of epinephrine in dogs as the standard epinephrine IM 0.3 mg, a drug of choice for emergency treatment of anaphylaxis. See FIGS. 15 and 16.

This disclosure further encompasses the following embodiments.

Embodiment 1

A method for systemic delivery of a therapeutically effective amount of epinephrine to a subject, comprising orally administering dipivefrin or a pharmaceutically acceptable salt thereof to the subject.

Embodiment 2

A method for treating a condition responsive to epinephrine in a subject comprising orally administering a therapeutically effective amount of dipivefrin or a pharmaceutically acceptable salt thereof to the subject.

Embodiment 3

The method of embodiment 2, wherein the condition is a breathing difficulty.

TABLE 12

Summary of PK analysis results in beagle dogs (data presented as mean ± SEM)

| Test articles | Dose | $C_{max}$ (ng/ml) | $T_{max}$ (min) | $AUC_{last}$ (ng min/ml) |
|---|---|---|---|---|
| Dipivefrin HCl orally dissolving tablet | 63.5 mg | 46.60 ± 11.22 | 16.7 ± 3.3 | 2325.72 ± 459.60 |
| Dipivefrin HCl orally dissolving tablet | 5 mg | 6.10 ± 2.65 | 30.0 ± 5.8 | 289.16 ± 76.14 |
| Epinephrine IM | 0.3 mg | 3.01 ± 1.43 | 25.0 ± 17.6 | 147.37 ± 39.41 |

Embodiment 4

The method of embodiment 3, wherein the breathing difficulty is anaphylaxis, asthma, bronchitis, emphysema, croup, or a respiratory infection.

Embodiment 5

The method of embodiment 2, wherein the condition is anaphylaxis.

Embodiment 6

The method of embodiment 5, wherein the treatment of anaphylaxis comprises relieving at least one symptom of anaphylaxis in the subject.

Embodiment 7

The method of embodiment 5, wherein the treatment of anaphylaxis comprises reducing the severity of anaphylaxis or inhibiting the onset of anaphylaxis in the subject following exposure of the subject to an allergen.

Embodiment 8

The method of embodiment 2, wherein the condition is cancer.

Embodiment 9

The method of embodiment 8, wherein the cancer is skin cancer, brain cancer, a glioma, a sarcoma, breast cancer, lung cancer, non-small-cell lung cancer, mesothelioma, appendicular cancer, a genitourinary cancer, a renal cell carcinoma, prostate cancer, bladder cancer, testicular cancer, penile cancer, cervical cancer, ovarian cancer, von Hippel Lindau disease, a head and neck cancer, a gastrointestinal cancer, a hepatocellular carcinoma, gallbladder cancer, esophageal cancer, gastric cancer, colorectal cancer, pancreatic cancer, a neuroendocrine tumor, a thyroid tumor, a pituitary tumor, an adrenal tumor, a hematological malignancy, a lymphoma, a leukemia, or a combination thereof.

Embodiment 10

The method of embodiment 8, wherein the cancer is skin cancer, and the skin cancer is a melanoma.

Embodiment 11

The method of any one of embodiments 8 to 10, wherein dipivefrin or its pharmaceutically acceptable salt is an adjunctive anticancer treatment and the method comprises administering at least one additional anticancer treatment to the subject.

Embodiment 12

The method of embodiment 2, wherein the condition is a microbial infection.

Embodiment 13

The method of embodiment 12, wherein the microbial infection is a bacterial, viral, fungal, or parasitic infection.

Embodiment 14

The method of embodiment 13, wherein the microbial infection is a viral infection.

Embodiment 15

The method of embodiment 14, wherein the viral infection is an influenza infection.

Embodiment 16

The method of claim 13, wherein the bacterial infection is a methicillin-resistant *Staphylococcus aureus* (MRSA) infection.

Embodiment 17

The method of any one of embodiments 12 to 16, wherein dipivefrin or its pharmaceutically acceptable salt is an adjunctive antimicrobial agent and the method further comprises administering at least one additional antimicrobial agent to the subject.

Embodiment 18

The method of embodiment 17 wherein the additional antimicrobial agent is an antibiotic.

Embodiment 19

The method of any one of embodiments 12 to 15, further comprising administering an antiviral agent to the subject.

Embodiment 20

The method of any one of embodiments 1 to 19, wherein the dipivefrin is racemic dipivefrin.

Embodiment 21

The method of any one of embodiments 1 to 19, wherein the dipivefrin is L-dipivefrin.

Embodiment 22

The method of any one of embodiments 1 to 19, wherein dipivefrin hydrochloride is administered.

Embodiment 23

The method of any one of embodiments 1 to 19, wherein L-dipivefrin hydrochloride is administered.

Embodiment 24

The method of any one of embodiments 1 to 19, wherein the dipivefrin is isotopically labeled dipivefrin or a pharmaceutically acceptable salt thereof.

Embodiment 25

The method of any one of embodiments 1 to 19, wherein the dipivefrin or salt thereof, is administered as oral solution, a tablet, or a capsule.

Embodiment 26

The method of embodiment 25, wherein the dipivefrin or salt thereof is administered as an oral aqueous solution.

Embodiment 27

The method of embodiment 25, wherein the dipivefrin or salt thereof is administered as an orally dissolving tablet or an orally disintegrating tablet.

Embodiment 28

The method of any one of embodiments 1 to 27, wherein the dipivefrin or salt thereof is administered as a dosage form comprising 0.01 mg to 150 mg, 0.01 mg to 100 mg, 0.01 mg to 50 mg, 0.1 mg to 20 mg, 0.1 mg to 10 mg, 0.1 mg to 5 mg, 0.1 mg to 3 mg, 2.5 mg, 2 mg, or 1.5 mg dipivefrin.

Embodiment 29

The method of any one of embodiments 1 to 27 wherein the therapeutically effective amount of dipivefrin or salt thereof is an amount sufficient to provide an epinephrine plasma $C_{max}$ of 0.1 to 50.0 ng/mL in the subject.

Embodiment 30

The method of any one of embodiments 1 to 27 wherein the therapeutically effective amount of dipivefrin or salt thereof is an amount sufficient to provide a pharmacokinetic profile substantially equivalent to the epinephrine pharmacokinetic profile of an US FDA-approved injectable dosage form comprising epinephrine, when the US FDA-approved injectable dosage form is administered either intramuscularly or subcutaneously.

Embodiment 31

The method of embodiment 30 wherein the US FDA-approved dosage form comprises 0.3 mg epinephrine and is administered intramuscularly.

Embodiment 32

The method of embodiment 30 wherein the US FDA-approved dosage form comprises 0.15 mg epinephrine and is administered intramuscularly.

Embodiment 33

The method of embodiment 30 wherein the US FDA-approved dosage form comprises 0.1 mg epinephrine and is administered intramuscularly.

Embodiment 34

The method of embodiment 30 wherein the US FDA-approved dosage form comprises 0.3 mg epinephrine and is administered subcutaneously.

Embodiment 35

The method of embodiment 30 wherein the US FDA-approved dosage form comprises 0.15 mg epinephrine and is administered subcutaneously.

Embodiment 36

The method of embodiment 30 wherein the US FDA-approved dosage form comprises 0.1 mg epinephrine and is administered subcutaneously.

Embodiment 37

The method of any one of embodiments 1 to 27 or 29-36 wherein the method provides a therapeutically effective amount of epinephrine within 30 minutes of administration, within 15 minutes of administration, within 10 minutes of administration, or within 5 minutes of administration.

Embodiment 38

The method of any one of embodiments 1 to 27 or 29 to 37 wherein the method provides a $T_{max}$ of epinephrine within 45 minutes of administration.

Embodiment 39

An orally dissolving tablet comprising dipivefrin or a dipivefrin salt in a matrix capable of dissolving in the oral cavity in 2 minutes or less.

Embodiment 40

The tablet of embodiment 39, wherein the tablet comprises dipivefrin HCl.

Embodiment 41

The tablet of embodiment 39 or 40, wherein the tablet additionally comprises a water soluble polymer and a sweetener.

Embodiment 42

The tablet of embodiment 41 wherein the water soluble polymer is gelatin, HPMC, or a combination of the foregoing.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). The values described herein are inclusive of an acceptable error range for the particular value as determined by one of ordinary skill in the art, which will depend in part on how the value is measured or determined, i.e., the limitations of the measurement system. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for systemic delivery of a therapeutically effective amount of epinephrine to a subject, wherein the subject is a human or dog, comprising orally administering dipivefrin or a pharmaceutically acceptable salt thereof to the subject.

2. A method for treating a condition responsive to epinephrine in a subject, wherein the subject is a human or dog, the method comprising administering, as an oral dosage form, a therapeutically effective amount of dipivefrin or a pharmaceutically acceptable salt thereof to the subject.

3. The method of claim 2, wherein the condition is anaphylaxis, asthma, bronchitis, emphysema, croup, or a respiratory infection.

4. The method of claim 3, wherein the condition is anaphylaxis.

5. The method of claim 4, wherein the treatment of anaphylaxis comprises reducing the severity of anaphylaxis or inhibiting the onset of anaphylaxis in the subject following exposure of the subject to an allergen.

6. The method of claim 2, wherein the condition is cancer.

7. The method of claim 6, wherein the cancer is skin cancer, and the skin cancer is a melanoma.

8. The method of claim 2, wherein the condition is a microbial infection and the microbial infection is a bacterial, viral, fungal, or parasitic infection.

9. The method of claim 8, wherein the microbial infection is an influenza infection.

10. The method of claim 8, wherein the microbial infection is a methicillin-resistant *Staphylococcus aureus* (MRSA) infection.

11. The method of claim 2, wherein the dipivefrin is racemic dipivefrin or racemic dipivefrin hydrochloride.

12. The method claim 2, wherein the dipivefrin is L-dipivefrin or L-dipivefrin hydrochloride.

13. The method of claim 2, wherein the dipivefrin or salt thereof is administered as an orally dissolving tablet or orally disintegrating tablet.

14. The method of claim 2, wherein the oral dosage form comprising dipivefrin or salt thereof, provides an epinephrine $T_{max}$ of 45 minutes or less and an epinephrine plasma $C_{max}$ of 0.1 to 50.0 ng/mL when administered to the subject.

15. The method of claim 2, wherein the therapeutically effective amount of dipivefrin or salt thereof is an amount sufficient to provide a pharmacokinetic profile substantially equivalent to the epinephrine pharmacokinetic profile of an US FDA-approved injectable dosage form comprising epinephrine, when the US FDA-approved injectable dosage form, comprising 0.3 mg epinephrine, 0.15 mg epinephrine, or 0.1 mg epinephrine is administered either intramuscularly or subcutaneously.

16. The method of claim 2, wherein the method provides a $T_{max}$ of epinephrine within 45 minutes of administration.

17. The method of claim 4, wherein the treatment of anaphylaxis comprises relieving at least one symptom of anaphylaxis in the subject.

18. The method of claim 2, wherein L-dipivefrin hydrochloride is administered.

19. The method of claim 2, wherein L-dipivefrin hydrochloride is administered as a dosage form comprising 1 mg to 10 mg dipivefrin.

20. A method of treating anaphylaxis in a subject, wherein the subject is a human or dog and the method comprises orally administering to the subject an L-dipivefrin hydrochloride oral dosage form comprising from 0.1 to 20 mg of L-dipivefrin.

21. The method of claim 20, wherein the oral dosage form is an orally dissolving tablet or orally disintegrating tablet.

22. The method of claim 21 wherein the orally dissolving tablet or orally disintegrating tablet is placed on the tongue, under the tongue, or in the buccal cavity.

23. A method of treating anaphylaxis in a subject, wherein the subject is a human or dog, comprising orally administering not more than 63.5 mg L-dipivefrin hydrochloride to provide an epinephrine $T_{max}$ of less than 45 minutes and an epinephrine plasma $C_{max}$ of 0.1 to 50 ng/mL in the subject.

24. The method of claim 22, wherein the method provides a therapeutically effective amount of plasma epinephrine within 10 minutes of administration.

25. The method of claim 2, wherein the oral dosage form is selected from an oral solution or suspension, a tablet, a capsule, a sprinkle or a powder.

26. The method of claim 25, wherein the tablet is an orally dissolving tablet or orally disintegrating tablet.

27. A method for treating anaphylaxis in a subject, wherein the subject is a human or dog, the method comprising administering, as an oral dosage form, a therapeutically effective amount of L-dipivefrin hydrochloride to the subject.

* * * * *